(12) United States Patent
Smith

(10) Patent No.: US 6,764,693 B1
(45) Date of Patent: Jul. 20, 2004

(54) FREE RADICAL QUENCHING COMPOSITION AND A METHOD TO INCREASE INTRACELLULAR AND/OR EXTRACELLULAR ANTIOXIDANTS

(75) Inventor: Milton G. Smith, Washington, DC (US)

(73) Assignee: Amaox, Ltd., Lawton, MI (US)

( * ) Notice: Subject to any disclaimer, the term of this patent is extended or adjusted under 35 U.S.C. 154(b) by 1676 days.

(21) Appl. No.: 07/989,593

(22) Filed: Dec. 11, 1992

(51) Int. Cl.[7] .............................................. A61K 9/127
(52) U.S. Cl. ...................... 424/450; 424/400; 424/422; 424/434; 424/45
(58) Field of Search .................. 424/450, 2.2, 702, 424/45, 641, 422, 630, 434, 626, 400; 514/356, 458, 474, 725

(56) References Cited

U.S. PATENT DOCUMENTS

| | | |
|---|---|---|
| 3,069,319 A | 12/1962 | Stearns et al. |
| 3,499,914 A | 3/1970 | Kliak et al. |
| 3,957,966 A | 5/1976 | Valan |
| 4,144,325 A | 3/1979 | Voyt |
| 4,241,054 A * | 12/1980 | Volpenhein |
| 4,454,125 A | 6/1984 | Demopoulos |
| 4,466,838 A | 8/1984 | Heeb et al. |
| 4,487,297 A | 12/1984 | Hoffman, Jr. |
| 4,619,794 A | 10/1986 | Hauser |
| 4,668,516 A | 5/1987 | Duraffourd et al. |
| 4,695,452 A | 9/1987 | Gannis et al. |
| 4,818,521 A | 4/1989 | Tamabuchi |
| 4,826,814 A | 5/1989 | Sawayama et al. |
| 4,847,297 A | 7/1989 | Chandra |
| 4,849,452 A | 7/1989 | Dulce et al. |
| 4,880,779 A | 11/1989 | Gallaher |
| 4,885,157 A | 12/1989 | Fiaschetti |
| 4,892,733 A | 1/1990 | Bichon et al. |
| 4,900,550 A | 2/1990 | Lowry |
| 4,983,626 A | 1/1991 | Ismail |
| 4,987,122 A | 1/1991 | Laerum |
| 5,000,945 A | 3/1991 | Kobayashi et al. |
| 5,006,333 A | 4/1991 | Saifer et al. |
| 5,011,695 A | 4/1991 | Dichtelmuller et al. |
| 5,013,556 A * | 5/1991 | Woodle ...................... 424/450 |
| 5,023,235 A * | 6/1991 | N'Guyen ..................... 424/401 |
| 5,032,585 A * | 7/1991 | Lichtenberger .............. 514/78 |
| 5,034,228 A * | 7/1991 | Meybeck et al. ........... 424/401 |
| 5,049,388 A | 9/1991 | Knight et al. |
| 5,049,390 A | 9/1991 | Wojdani |
| 5,049,391 A | 9/1991 | Suzuki et al. |
| 5,132,113 A * | 7/1992 | Luca |
| 5,326,757 A * | 7/1994 | Demopoulos |
| 5,431,924 A * | 7/1995 | Ghosh |

FOREIGN PATENT DOCUMENTS

| | | |
|---|---|---|
| EP | A-0 391 218 | 10/1990 |
| EP | A-0 455 386 | 11/1991 |

OTHER PUBLICATIONS

Biology, By N.A. Cambell, pp. 810–813, 1981. The Benjamin/Cummings Publishing Company, Inc.*

Biochemistry, The molecular basis of cell structure and function by Lehninger, pp. 204–206, 1970, Worth Publishers, Inc.*

(List continued on next page.)

Primary Examiner—Thurman K. Page
(74) Attorney, Agent, or Firm—Greenberg Traurig, LLP; Michel Morency; John M. Garvey

(57) ABSTRACT

A free radical quenching composition is disclosed comprising a liposome containing at least two antioxidants selected from the following group: beta-carotene, vitamin E, vitamin C, glutathione, niacin, and optionally at least one trace metal (Zn, Se, Cr, Cu, Mn). Also disclosed is a method for reducing the undesirable side effects of free radicals in a mammal by administering to a mammal in need of such antioxidants an effective amount of liposomes containing at least two antioxidants.

12 Claims, 18 Drawing Sheets

Activated leukocytes liberating oxidants, but cellular membrane is protected by the prescience of fat and water soluble antioxidants.

OTHER PUBLICATIONS

Free radicals in Biology and Medicine. Ed. by Halliwell & Gutteridge, 1991.*

Pelle, Vitamin E, Biochemistry v Health Implications. 570, 1989.*

Packer, Proc. Soc. Exp. Bia. Med. 200, 1992.*

Webster's Dictionary, 1988 Ondrox advertisement.*

Advertisement for Ondrox multi–antioxidant formulation, 1992.

Advertisement for Avon Advanced Night Support—1993.

Liebler, D.C., et al., "Redox cycles of vitamin E . . . ", Biochemistry (1989), vol. 28, pp. 9772–9777.

Motoyama, T., et al., "Synergistic inhibition of oxidation . . . ", Archives of Biochemistry and Biophysics (1989), vol. 270, pp. 655–661.

Roederer, M., et al., "N–acetylcysteine: A new approach to anti–HIV therapy", AIDS Research and Human Retroviruses (1992), vol. 8, pp. 209–217.

Staal, F.R.T., et al., "Glutathione deficiency and human . . . ", The Lancet (1992), vol. 339, pp. 909–912.

Database WPI Week 8737 Derwnet Publication Ltd., London, GB; An 87–259765XP002037755 & JP 62178521 A (Terumo Corp), Aug. 5, 1987.

Archives of Biochemistry and Biophysics, vol. 270, No. 2, p. 655–661, 1989, (Motoyama) "Synergistic Inhibition of Oxidation in Dispersed Phosphatidylcholine Liposomes by a Combination of Vitamin E and Cysteine".

Free Radicals in Biology and Medicine, 2nd. Edition, 1991 (halliwell & Gutteridge), p. 422–438.

*Liposomal Antioxidants Provide Prolonged Projection Against Acute Respiratory Distress Syndrome*; J. Fan. et al., *Surgery*, vol. 128, No. 2, Aug., 2000; pp. 332–338.

The American Journal of Medicine, Proceeding of a Symposium on Oxidants and Antioxidants: Pathophysiologic Determinants and Therapeutic Agents, vol. 91 (3C), Sep. 30, 1991, title page, pp. 39–44S, 79–85S, 118–121S and 145S.

1991 Vitamin E Abstracts, title page, pp. 89–93 and 117–135.

Halliwell, B., and J.M.C. Gutteridge, Free Radicals in Biology and Medicine, 2nd Edition, 1991, title page, pp. 123–133, 263–266, 284–286 and 416–494.

* cited by examiner

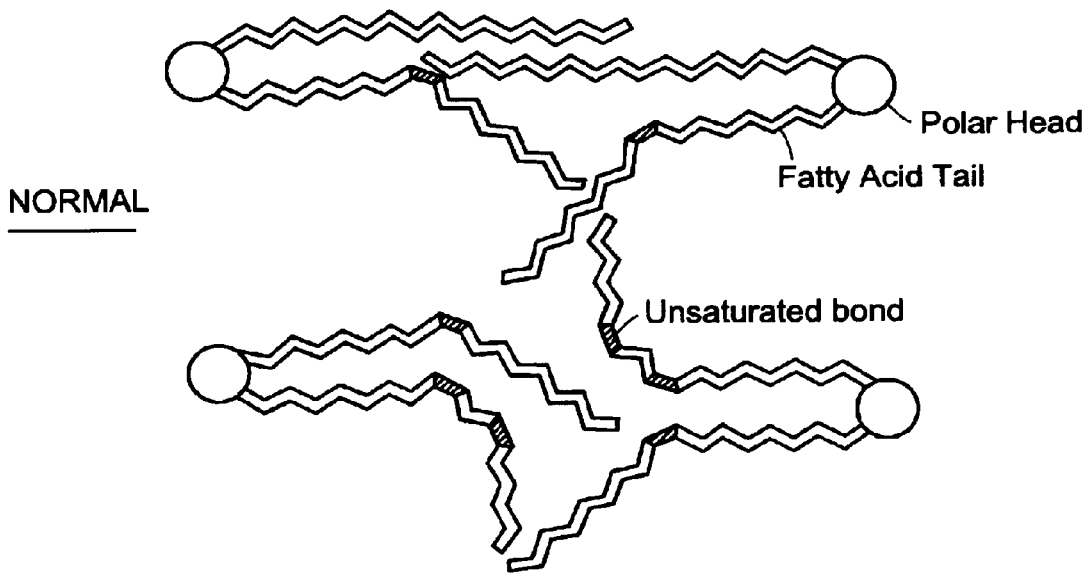
NORMAL
Polar Head
Fatty Acid Tail
Unsaturated bond
Consequences of Oxidative Agents Attacking Membranes
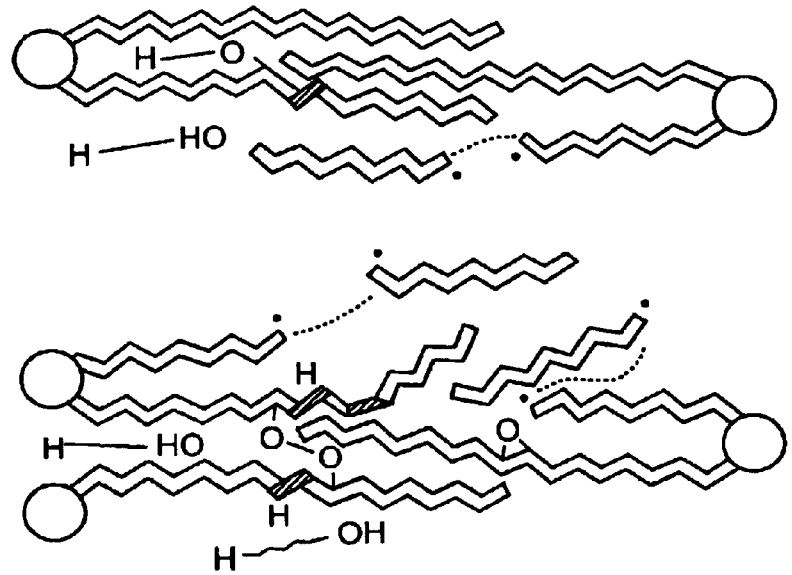
FIG. 1

No liberation of oxidants

Oxidants liberated into the microenvironment, and subsequently attacking liposomes.
Antioxidants also liberated into the microenvironment, after rupture of liposomes.

The liposome may undergo peroxidation on entrance through the cell membrane or within the cell itself Liposomes in the proximity of a cellular membrane undergoing peroxidation. The liposomes once adjacent to the membrane, would then also undergo peroxidation with release of antioxodants. The anti-oxidants will quench the free radicals and abate futher membrane damage.

Oxidants occuring within the cell membrane attack the liposomal membrane. Oxidants would then be erradicated preventing further tissue damage.

A- adsorbed liposome

B- Liposome undergoing endocytosis

C- Liposome undergoing lipid exchange

D- Fused liposome

E- Cell membrane undergoing peroxidation with subsequent peroxidation of liposomes (not shown, see Fig.6)

Aqueous-Lipid Interface    Lipid Phase    Aqueous Phase

The dark areas are the aqueous phase, and the light areas are lipid. Lipid soluble antioxidants would be found in the lipid phase and water soluble antioxidants would be found in the aqueous phase.

FIG. 12

| FIG. 12A | FIG. 12B |

T cell function:

- induction of NK cell function

- induction of cytotoxic T cell function

- secretion of factors which induce non-lymphoid cell function

- induction of suppressor cell function

- secretion of growth and differention factors for lymphoid cells

- secretion of hematopietic colony stimulating factors

- activation of macrophages

- induction of B cell function

Glutathione regulates:

- CD4 and CD8 receptors

- PGE2 synthesis (& other PGs)

- macrophage phagocytosis

- leukotriene C production

- T cell proliferation

- glutathione peroxidase function in macrophages

- DNA synthesis

- blast formation

- IL-2 receptors (alpha chain) → (A)

- NF-KB transcription for cytokines and proteins involved in the inflammatory process

- the affinity of NF-KB to DNA

- the dimerization of the HIV tat protein or the conformational changes in the tat protein(?)

FIG. 12A

| Tumor necrosis factor-α induces free radicals: | Il-2 supports: | Interleukin-6: |
|---|---|---|
| • directly in susceptible tumor cells | • proliferation of stimulated T cells | • primes leukocytes to produce free radicals |
| • indirectly by stimulating leukocytes | • proliferation of B lymphocytes | |
| • indirectly by releasing arachidonic acid | Il-2 augments the reactivity of: | |
| • indirectly by releasing lysosomes | • cytolytic T cells | |
| Tumor necrosis α is stimulated by: | • NK cells | |
| • free radicals  (A) | • stimulates the production of IFN-gamma and monocytes | |
| | • induction of lymphokine-activated killer cells | |
| | IL-1 regulates | |

(found to be increased in AIDS and rheumatoid arthritis)

Glutathione decreased in AIDS
TNF-alpha increased in AIDS, Sepsis, Burns
IL-6 increased in AIDS

FIG. 12B

AA Metabolites = Arachidonic Acid metabolites

Prostaglandin Metabolites; Enzymes and Their Inhibitors

Key to abbreviations:
- PGG2 - Prostaglandin G2
- PGH2 - Prostaglandin H2
- TXA2 - Thromboxane A2
- PGI2 - Prostaglandin I2
- PGE2 - Prostaglandin E2
- PGF2 - Prostaglandin F2
- 15-Keto-PG's - 15- Keto- Prostaglandins
- 12-HPETE - 12- Hydroperoxy eicosatetraenoic acid
- 12-HETE - 12- Hydroxyeicosate-traenoic acid
- 5-HPETE - 5- Hydroperoxy eicosatetraenoic acid
- 5-HETE - 5- Hydroxyeicosate-traenoic acid
- LTA4 - Leukotriene A4
- LT's - Leukotrienes (types B4, C4, D4, E4)

| Enzymes | Enzyme Inhibitors | |
|---|---|---|
| Phospholipase A2 | Alpha-tocopherol | (fat soluble) |
| Phospholipase C | Nicotinic acid | (Water soluble) |
| Cyclooxygenase | Alpha-tocopherol and beta-carotene | (fat soluble) |
| Lipooxygenase | Glutathione and ascorbic acid | (Water soluble) |

FIG. 16

Activated leukocytes liberating oxidants, but cellular membrane is protected by the prescience of fat and water soluble antioxidants.

FREE RADICAL QUENCHING COMPOSITION AND A METHOD TO INCREASE INTRACELLULAR AND/OR EXTRACELLULAR ANTIOXIDANTS

BACKGROUND AND INTRODUCTION

The present invention relates to a free radical quenching composition comprising a liposome containing at least two antioxidants selected from the following groups: beta-carotene, vitamin E, vitamin C, glutathione, niacin, and optionally trace metals (Zn, Se, Cr, Cu, Mn). The present invention also concerns a method for reducing the undesirable side effects of free radicals in a mammal by administering to a mammal in need of such antioxidants an effective amount of liposomes containing at least two antioxidants.

Previously there has not existed a composition or method for increasing the entire spectrum of non-enzymatic antioxidants in either the extracellular and/or intracellular milieu, either simultaneously or sequentially or selectively. Previous experiments that have attempted to alter free radical reactions in mammals have increased antioxidant levels by diet, intraperitoneal injections, or by the addition of one or two non-enzymatic or enzymatic antioxidants (but not within the same liposome).

Turrens and others (J. Clin. Invest; Vol. 73, 1984:87–95) injected mice with liposomes containing superoxide dismutase and catalase in an effort to examine its possible protective effects against oxygen toxicity. There were several beneficial effects described for those rats injected with liposomes containing these antioxidant enzymes: increased survival, less fluid in the pleural cavity, an increase of superoxide dismutase and catalase concentrations of 1.7 and 3.1 fold respectively, superoxide activity increased over controls. It was also noted that the half lives for the liposome entrapped antioxidants were also markedly prolonged in comparison to the injection of free enzymes.

The antioxidant glutathione (GSH) was entrapped in liposomes and administered intravenously to rats. Wendel et al. demonstrated significant hepatic protection from lipid peroxidation which had been induced by paractomel. There was significant uptake of the glutathione entrapped in liposomes in the liver and spleen. This was the first demonstration of the efficacy of liposome encapsulated non-enzymatic antioxidant levels being increased in vivo. Free GSH intravenously administered has a $t_{1/2}$ of approximately 1.6 minutes; in contrast, intravenously administered liposomes encapsulating GSH are postulated to have a longer half life.

These previous methods of increasing cellular antioxidant levels have serious shortcomings with little use in the clinical setting. Previous works involving the administration of antioxidants have failed to appreciate the potpourri of different oxidants generated in various pathological conditions.

SUMMARY OF THE INVENTION

In order for a composition to be effective in the elimination of a variety of free radicals, it must contain antioxidants that are specific for such free radicals. The present invention concerns a composition that contains at least two members of the following: beta-carotene, alpha-tocopherol (vitamin E), ascorbic acid (vitamin C), glutathione, niacin, with or without trace metals, all of which are contained in the same liposome or in a multiple liposomal arrangement. The liposomes participate in the pathologic free radical reactions by undergoing peroxidation, thereby bursting and releasing the antioxidants.

The present invention also relates to a method of delivering non-enzymatic antioxidants and a method for reducing the undesirable side effects of free radicals in a mammal.

BRIEF DESCRIPTION OF THE DRAWINGS

FIG. 1—free radical attack on membranes.

FIG. 12—cytokines and antioxidant regulators.

FIG. 16—prostaglandin metabolites, enzymes and their inhibitors.

DETAILED DESCRIPTION OF THE INVENTION

Figure 2:
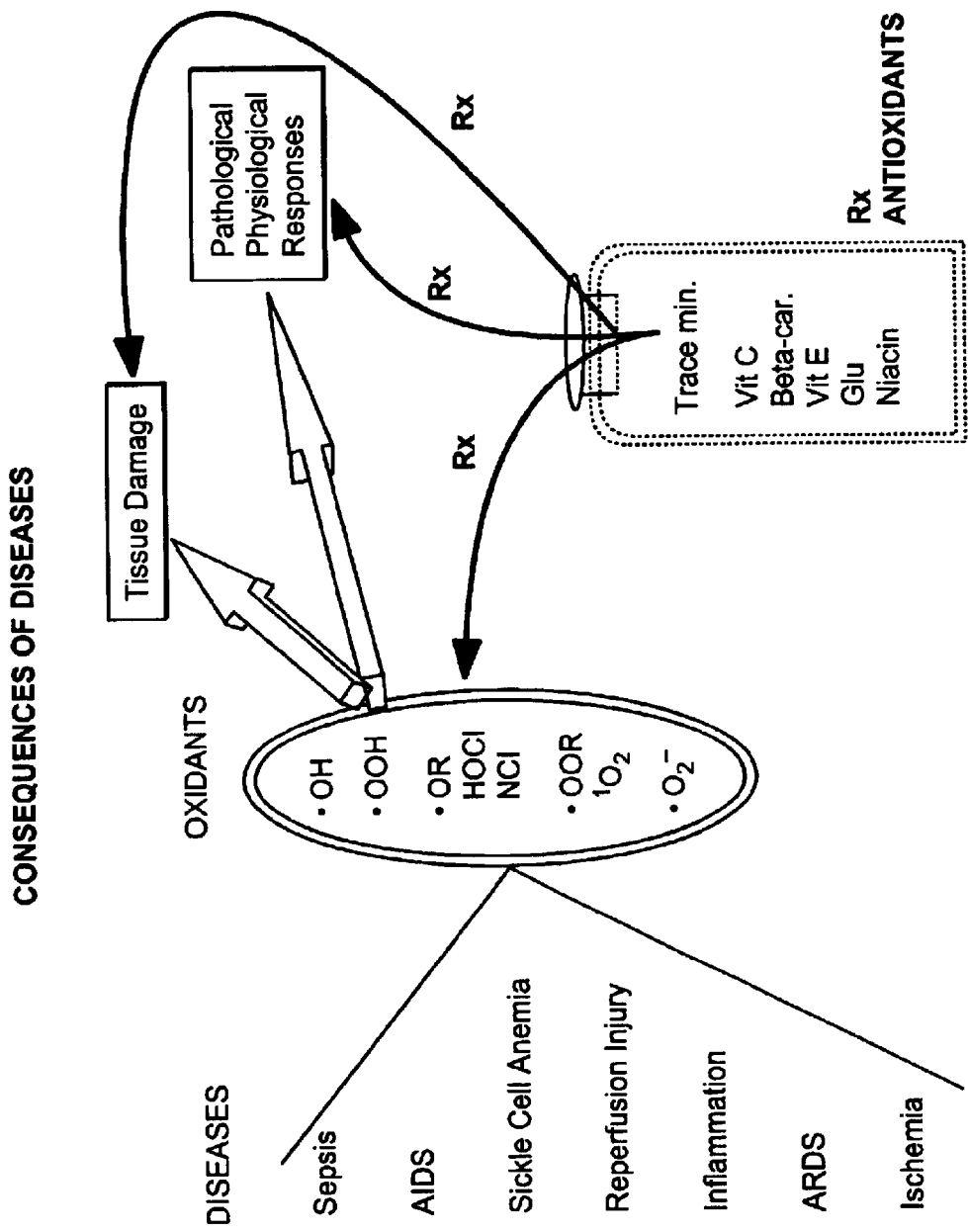
FIG. 2—diagram of diseases, oxidant products of diseases, and antioxidants.

Amphipathic antioxidants are used as a medical composition to quench free radical reactions and to increase both intracellular and/or extracellular antioxidant concentrations. The liposomal-antioxidant combination in this invention is inseparable, that is, the function of the liposomes in this invention is more than simply a carrier or vehicle for the amphipathic antioxidants, but can and often does participate itself in the free radical reaction occurring at a given site. This concept of the liposomes actually participating in the biochemical reaction (via peroxidation by free radicals) is a significant departure from the prior art. In the prior art, liposomes were merely carriers for a drug, pro-enzyme, vitamin, hormone, etc.

There have been numerous experiments that show liposomes undergoing peroxidation after being exposed to a free radical generating source. The source of oxidants (the subsets of oxidants are free radicals) may be enzymatic, radiation, leukocytes, chemical, etc. These oxidants attack the unsaturated bond structures in the liposomal membranes, resulting in peroxidation and consequent lysis of the liposomes. This concept of the lysis of liposomes resulting in the leakage of its contents after peroxidation was disclosed in the work of Sepe and Clark.

The liposomes of the present invention can be modified in various ways. The liposomes may be modified to vary the number of unsaturated bonds present which is proportional to its susceptibility to free radical attack and subsequent peroxidation of its membrane. Liposomes can be further modified in several ways, such as the charge on the membrane, the presence of monoclonal antibodies, cross linking, etc., and the present invention includes such modifications. Depending on the liposomal composition carrying the amphipathic antioxidants, it would seek its given target tissue (e.g., the lypmhoreticular system). Given that free radical reactions were occurring at that site, the liposomes, once in the proximity of the free radical reaction, would themselves undergo peroxidation. The free radical attack on the bilamellar membrane of the liposome would result in its disruption and consequently the delivery of its payload. Once the liposomes are disrupted and their payload delivered, the fatty acids and oxidized antioxidants would be metabolized to harmless substances by the host in the usual fashion.

Liposomes offer significant advantages for the delivery of free antioxidants of the extracellular milieu and the cytosol. The amphipathic antioxidants contained in the liposomes of the present invention are hydorphilic or hydrophobic. Administration of these antioxidants in the clinical setting would be cumbersome and impractical if they were not delivered by the vehicle of the present liposomes. Prior to this invention there has not been any treatment proposed for clinical utilization of amphipathic antioxidants entrapped in liposomes.

Previously there has not been an amphipathic antioxidant system such as the one proposed. Others have been antioxidants of either the enzymatic (e.g., glutathione peroxidase, myeloperoxidase, superoxide dismutase, and catalase) or non-enzymatic type (singularly) in an effort to ameliorate pathologic free radicals or to increase tissue antioxidant levels. There has not been any system whereby at least two of the antioxidants vitamin E, ascorbic acid, beta-carotene, glutathione, or niacin (or niacinamide), and as an option the addition of trace metals (e.g., selenium, manganese, copper, zinc, chromium), have been used simultaneously in the same liposome with the intent of increasing extracellular and/or intracellular levels of antioxidants. The antioxidants are utilized in their reduced state.

In carrying out this invention, the active component consisting of amphipathic antioxidants (AMAOX) (i.e., vitamin E, vitamin C, beta-carotene, glutathione, and niacinamide, and optionally trace metals), may be administered in any permutation of combinations of two or more per liposome. They can be administered consecutively or simultaneously in any permutation in a liposome population (with or without the addition of trace metals to the other amphipathic antioxidants and niacin):

vitamin E+vitamin C
vitamin E+vitamin C+beta-carotene
vitamin E+vitamin C+beta-carotene+glutathione
vitamin E+vitamin C+beta-carotene+glutathione+trace metals
vitamin E+vitamin C+beta-carotene+glutathione+trace metals+niacin
vitamin C+beta-carotene
vitamin C+beta-carotene+glutathione
vitamin C+beta-carotene+glutathione+trace metals
vitamin C+beta-carotene+glutathione+trace metals+niacin
vitamin C+beta-carotene+glutathione+trace metals+niacin+vitamin E
beta-carotene+glutathione
beta-carotene+glutathione+trace metals
beta-carotene+glutathione+trace metals+niacin
beta-carotene+glutathione+trace metals+niacin+vitamin E
beta-carotene+glutathione+trace metals+niacin+vitamin E+vitamin C
glutathione+trace metals
glutathione+trace metals+niacin
glutathione+trace metals+niacin+vitamin E
glutathione+trace metals+niacin+vitamin E+vitamin C
glutathione+trace metals+niacin+vitamin E+vitamin C+beta carotene
trace metals+niacin
trace metals+niacin+vitamin E
trace metals+niacin+vitamin E+vitamin C
trace metals+niacin+vitamin E+vitamin C+beta-carotene
trace metals+niacin+vitamin E+vitamin C+beta-carbotene+glutathione
niacin+vitamin E
niacin+vitamin E+vitamin C
niacin+vitamin E+vitamin C+beta-carotene
niacin+vitamin E+vitamin C+beta-carotene+glutathione
niacin+vitamin E+vitamin C+beta-carotene+glutathione+trace metals They preferably may be administered as a group (consisting of vitamin E, glutathione, ascorbic acid, beta-carotene, and niacin, with or without the use of trace metals) within the same liposome.

Alternatively there can be utilized simultaneously or consecutively a heterogeneous population of liposomes. For example, one type of liposome (e.g., containing glutathione, vitamin C can be utilized with another type of liposome (e.g., containing vitamin E, beta carotene, copper, selenium); or a liposome population (e.g., liposomes containing vitamin C, liposomes containing niacin, liposomes containing beta-carotene) can be utilized with another liposome population (e.g., liposomes containing vitamin E, liposomes containing glutathione, liposomes containing trace metals(s)).

Trace minerals can be put into the liposome because certain enzymes utilize them. For example glutathione peroxidase uses selenium and glutathione, superoxide uses copper as a cofactor. It was postulated that in diseases where there is a large free radical load, there may be deficiencies of these trace elements in a particular microenvironment. The liposomal composition would allow delivery of AMAOX and trace minerals to enzymatic antioxidants (which may have been devoid of the cofactors). Delivery of the trace minerals may allow effective use of the enzymatic antioxidants by the host, in addition to the obvious use of the AMAOX. Since it known that zinc can upregulate superoxide dismutase and selenium can upregulate glutathione peroxidase, therefore increasing trace minerals in a given microenviornment would produce a net increase in enzymatic antioxidants in the microenvironment. A net increase in the enzymatic antioxidants and increasing amphipathic antioxidant would further reduce oxidative damage to tissue as wells as other deleterious effects due to free radicals.

The following is the structure for the fat/water soluble antioxidant, glutathione:

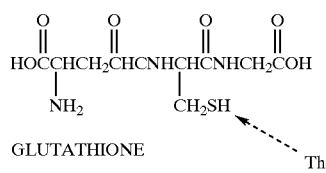

GLUTATHIONE

The active group in a free radical reaction

The following is the structure for the water soluble antioxidant, ascorbic acid:

The active group in a free radical reaction

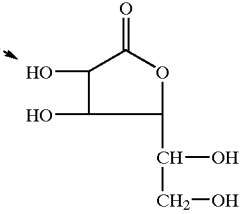

ASCORBIC ACID

The following is the structure for the water soluble antioxidant niacin:

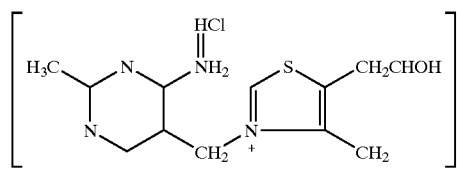

The following is the structure for the fat soluble antioxidant, provitamin A or beta carotene:

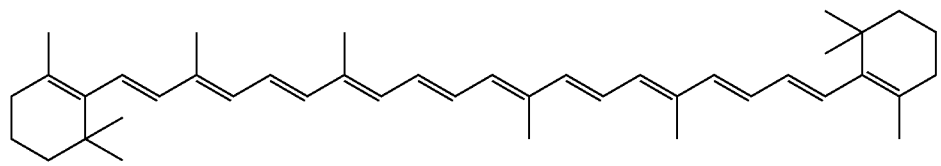

Quenches singlet oxygen by the following reaction:

$^1O_2$ + beta carotene $\longrightarrow$ $O_2$ + beta carotene (activated)

The following is the structure for the fat soluble antioxidant, alpha-tocopherol:

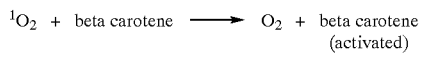

The following are the oxidant quenching reactions by alpha-tocopherol:

Tocopherol + RO* $\dashrightarrow$ Tocopherol* + ROH
(Lipid alkoxyl radical, reactive) (Tocopheryl quinone radical) (Lipid alcohol)

Tocopherol + ROO* $\dashrightarrow$ Tocopherol* + ROOH
(Lipid peroxyl radical) (Lipid Hydroperoxide)

Tocopherol-Ascorbate-Glutathione Redox Couplings

2 Tocopherol* + Ascorbate $\dashrightarrow$ 2 Tocopherol + Dehydroascorbate

Dehydroascorbate + 2 GSH $\xrightarrow{\text{DHA Reductase}}$ Ascorbic acid + GS-SG
(DHA) (Glutathione disulphide)

Oxidative Damage to Fatty Acids Occurs as Follows:

A. Peroxidation of fatty acids by hydroperoxide formation

| Carbon Atom numbers | 8 9 10 11 12 13 | | |
|---|---|---|---|
| Linoleic acid | 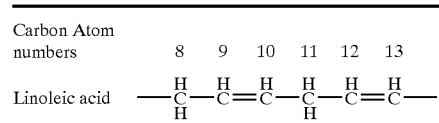 | +O—O | This oxygen molecule is a diradical and abstracts H from carbon #11, which is partly activated as a result of being in between two carbons with double bonds |
| Linoleic alkyl radical | 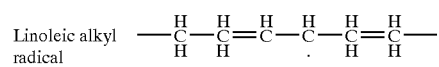 | Metal catalyzed +O—OH | There are now two radicals the hydroperoxy, .OOH, and the alkyl, R., on carbon #11 |
| Linoleic hydroperoxide | 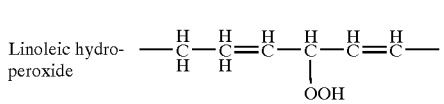 | Metal catalyzed | The two radicals have added together to form a new, two-electron covalent bond; this results in some of the molecules shifting their double bonds to become conjugated, and some of the cis bonds become trans |

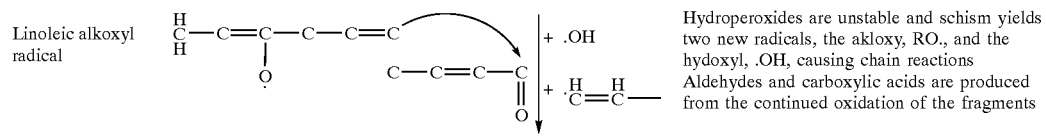

From Annals of The New York Academy of Sciences, vol 222, p 640–667, 1973

In biological tissues, oxidizing agents are produced from both intracellular and extracellular sources. In leukocyte free ischemia models, free radicals have been shown to occur (Zweir, et. al.). The oxidative phosphorylation chain present within mitochondria is one of the likely sources or intracellular free radicals, as well as xanthine-xanthine oxidase present in the endothelial lining of blood vessels. Extracellular sources of oxidants are due to leukocytes (the respiratory burst, the MPO-halide system, catalyst-lactoferritin), macrotyes/macrophages, eosinophils, free arachiodonic acid, polyunsaturated fatty acids undergoing peroxidation, lipid peroxides (e.g. cholesterol), denatured proteins containing metals, or simply free ionized metals which may act as catalysts (e.g. free copper, extravisated RBCs, etc.) and N-chloramines. In addition to the toxicity of free radicals, volatile hydrocarbons are also toxic; ethane and pentane are liberated when certain lipids undergo peroxidation in the prescience of metal catalysts (Riley, Calif., Cohen, G., Lieberman, M: Science 1974,183: 208–210; Tappel, A L, Dillard, C J: Fed Proc 1981, 40:174–178).

Oxidants include (but are not limited to) the following:
Reactive Oxygen Species:
$O_2^-$ Superoxide (can be reduced by vitamin E, beta carotene, glutathione, vitamin C)
$O_2$—Singlet Oxygen* (can be reduced by beta carotene and glutathione)
$OH^-$ Hydroxyl Radical* (can be reduced by glutathione, vitamin C)
OR Alkoxy radical (can be reduced by vitamin E, beta carotene, glutathione)
OOH Hydrogen Peroxyl Radical (can be reduced by vitamin E, glutathione, vitamin C)
OOR Alkyl peroxide* (can be reduced by beta carotene, vitamin C, vitamin E)
*Free radicals not able to be quenched by superoxide dismutase or catalase (or similar) enzymes
Other Oxidizing Agents:
HOX Hypohalous acids (X=chloride, bromine, iodide) (can be reduced by glutathione)
Z-AMINE Z=either chlorinated (Cl) or ammoniated (NH—) amine containing compounds (can be reduced by glutathione)
NO* Nitric Oxide (can be reduced by glutathione)
$NH_3$ Ammonia (can be reduced by glutathione)
Cyclooxygenase (can be inhibited by vitamin E, glutathione)
Phospholipase $A_2$ (can be inhibited by vitamin E)
Phospholipase C (can be inhibited by niacin)

All of the above antioxidants are naturally occurring and are found in virtually all mammalian cells. Antioxidants are of two types: enzymatic and non-enzymatic. They serve the purpose of chemically reacting with or degrading free radicals which may be produced under a variety of conditions, i.e. both during normal cellular functions and under pathological conditions. By the antioxidants reacting with the free radical it renders them a less potent oxidizing agent or completely harmless to cellular entities (e.g. DNA, membranes, proteins, carbohydrate moieties, etc.).

Scavengers of $H_2O_2$ and HOCl, e.g. ascorbic acid at >2 mM (ascorbate at <2 mM is a prooxidant) and glutathione, are able to inhibit the formation of chlorinated amines by eliminating their precursors from the above reaction. N—Cl formation can also be inhibited by inhibitors of myeloperoxidase. Singlet oxygen, alkyl peroxides, and hydroxyl radicals are quenched by non-enzymatic antioxidants.

There have been several instances wherein N-acetylcysteine (NAC) has been demonstrated to be an antioxidant. It has been shown to offer protection against the superoxide free radical in porcine aortic endothelial cells and protects animals against paracetamol hepatotoxicity. NAC also has been found to increase the intracellular concentration of GSH (glutathione). NAC reacts very slowly with superoxide or the hydrogen peroxide free radicals, so much so that it may be not significant. It can be seen from the rate constants that GSH is a more effective antioxidant against the hydroxyl radical in comparison to NAC (GSH K2=$8.8 \times 10^9$, NAC K2=$1.36 \times 10^{10}$ at a pH of 1.0). NAC will inhibit HOCl at physiological concentration in a 3:1 ratio (respectively).

Enzymatic antioxidants are not consumed in the reactions with free radicals, although they can be damaged under pathological conditions and consequently rendered non-functional. In the local cellular milieu, damaged enzymatic antioxidants would render that cellular environment compromised and subject to free radical attack. The disadvantage of administering enzymatic antioxidants to humans is (1) the possibility of allergic reactions (in the case of a bacterial or fungal derived enzyme) of varying degrees of severity; (2) the great cost of harvesting these enzymes; (3) the limitation of quantities of enzymatic antioxidants able to be administered at a given time (theoretically to avoid side effects such as serum sickness); (4) they serve a singular purpose (i.e., they react with only one type of oxidant); and (5) they do not quench all free radicals.

Non-enzymatic antioxidants can react with free radicals directly and become self-oxidized (therefore no longer available to quench free radicals); or one antioxidant may act as a reducing agent and another antioxidant oxidized in cyclical fashion (e.g., the interaction of ascorbic acid and alpha-tocopherol). Other non-enzymatic free radical scavengers have been used experimentally with varying results (e.g. mannitol, PBS, etc.); their clinical use is severely limited due to their toxocities.

Non-enzymatic antioxidants may be classified as either hydrophilic or hydrophobic. Alpha tocopherol and beta carotene are classified as hydrophobic, whereas ascorbic acid is hydrophilic. Glutathione shares characteristics of being both hydorphilic and hydrophobic. The characteristics of being either attracted to water (hydrophilic) or being repelled by water (hydrophobic) will determine the orientation of the particular antioxidant within the cytosol and/or membrane of the cell or liposome. Therefore free radical reactions occurring in the cytosol would be quenched by either glutathione or ascorbic acid, free radicals occurring within the membrane would be quneched by alpha-tocopherol and/or beta-carotene. Each of the non-enzymatic antioxidants react more favorably with certain free radicals as opposed to others. For example, singlet oxygen reacts with beta carotene; tocopherol is known to react with alkyl free radicals; glutathione and ascorbic acid are likely to be unselective in their reaction with various free radicals occurring within the cytosol.

The advantages of using a non-enzymatic antioxidant system for human use is that these antioxidants (1) are allogenic; (2) are readily utilized by all cells; (3) serve a multitude of cellular requirements; (4) have no significant toxicities; (5) once oxidized they are readily disposed of or are recycled depending on the particular requirement of the cell in question; (6) are able to quench all known biologically occurring pathological free radicals; and (7) can be given in large amounts.

There are numerous examples of liposomal peroxidation studies in the public domain, in particular the work of Seligman and Metamura. But one particularly cogent example is the work of Sepe and Clark. From Sepe and Clark's work it becomes obvious that the generation of hydrogen peroxide is essential to liposomal membrane lysis. Catalase inhibited peroxidation by the reduction of the hydrogen peroxide. The non-enzymatic antioxidants, beta-carotene and alpha-tocopherol, conferred protection against lipid peroxidation of the liposomes, as did the catalase.

Figure 3A:
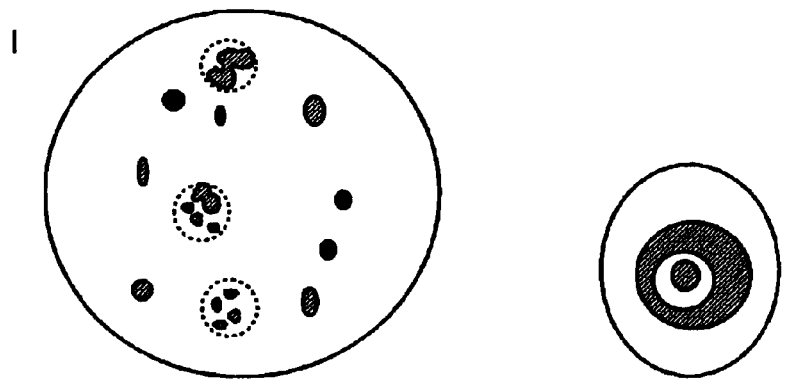
FIGS. 3A and 3B—amphipathic liposomal interaction with an activated leukocyte.
Figure 3B:
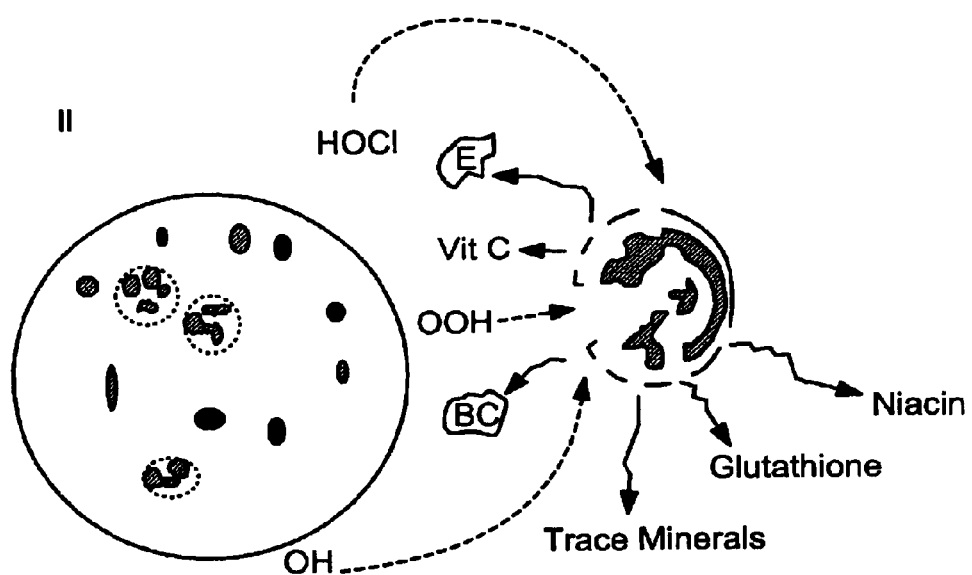
Figure 4:
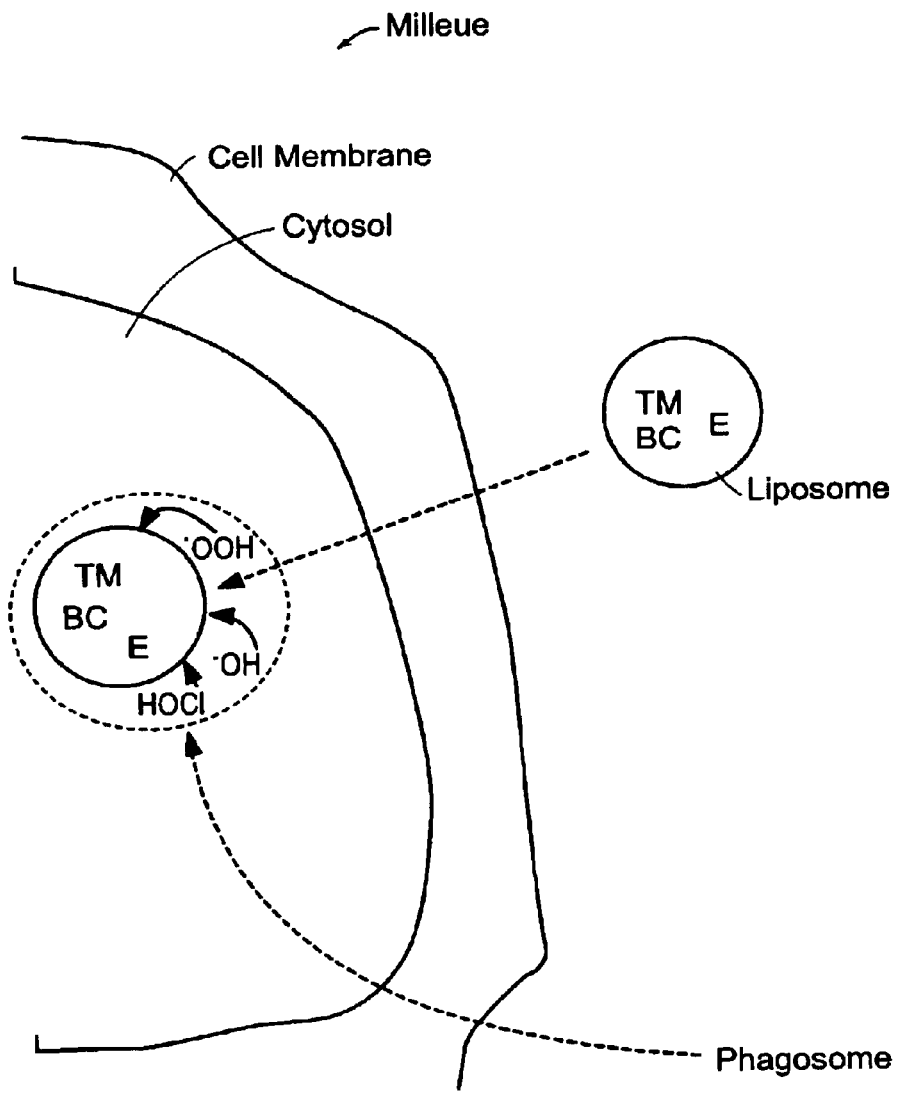
FIG. 4—oxidant interaction with liposomes.

Both enzymatic and non-enzymatic antioxidants have been shown to confer protection against oxidation in biological membranes. Sepe and Clark demonstrated how oxidants (generated by the activation of leukoxytes) occurring in the presence of biological membranes are able to induce membrane disruption. It is postulated that tissue damage occurs in a similar fashion, i.e., the oxidant's effect seen in regard to liposomal membrane lysis would appear to be similar to the oxidative damage which occurs in vivo in organ membranes (see FIG. 3).

The presence of both beta-carotene and alpha-tocopherol conferred protection against lipid peroxidation induced in artificial membranes (liposomes) by activated leukocytes (an extracellular source of oxidants). Cellular membrane protection against oxidant damage intracellularly (e.g., from mitochondria) and extracellularly could be achieved by artificially increasing the antioxidant level of the extracellular and intracellular milieu. It is postulated that the same effect is feasible in vivo by an increase in intracellular and/or extracellular antioxidants, depending on the desired effect which is to be brought about.

Unique to this invention is the combination of at least two antioxidants (alpha-tocopherol, beta-carotene, ascorbic acid, glutathione, and niacin, with or without trace metals) and their distribution within the liposomes. The lipophilic and hydrophilic antioxidants would undoubtedly interact with each other after exposure to a milieu which contained oxidants (Liebler, et al.; Motoyama, et. al.). Unique to this composition are the permutations and combinations of two or more of the above antioxidants in individual liposomes or in a multiple liposomal arrangement. Such liposomes can be applied to areas or body cavities where sites of inflammatory foci were present in an effort to decrease inflammation by decreasing free radicals. Increasing antioxidant levels in specific organs, by aerosol, intravenous, intraarterial, intrathecal, oral, topical, and subcutanoeus routes is also possible. Use of such liposomes can also increase the levels of systemic amphipathic antioxidants, increase the antioxidant levels of the extracellular space, and increase the antioxidant level of the intracellular space. The amphipathic antioxidant preparation can be applied to the skin as part of a vehicle, lotion, solution, aersol, or gel, in order to increase the antioxidant level in skin (inclusive or facial skin).

Unilamellar and multilamellar liposomes containing various combinations of the antioxidants (i.e., beta-carotene, vitamin E, vitamin C, glutathione, niacin, and optionally trace metals) can be prepared by methods known in the art. U.S. Pat. Nos. 4,897,308; 4,619,794; 5,049,388; and 5,049,390 are incorporated by reference in their entirety. *Kirk-Othmer Encyclopedia of Chemical Technology*, Third Edition, volume 15, pages 476–477 and volume 17, pages 306–307, and *Harper's Biochemistry*, 22nd Edition, pages 144–145 are incorporated by reference in their entirety.

For example, the liposomes can be made by dissolving a liposome forming compound or combination of such compounds in a suitable solvent. For example, lecithin (phosphatidylcholine), phosphatidylserine, or other suitable natural or synthetic phospholipids can be dissolved in a solvent such as chloroform or the like. Phospholipids suitable for making liposomes either alone or in combination can be selected from the following: Egg phosphatidylcholine (EPC); Dilauryloylphosphatidylcholine (DLPC); Dimyristoylphosphatidylcholine (DMPC); Dipalmitoylphosphatidylcholine (DPPC); Distearoylphosphatidylcholine (DSPC); 1-Myristoyl-2-palmitolyphosphatidylcholine (MPPC); 1-Palmitoyl-2-myristolyl phosphatidylcholine (PMPC); 1-palmitoyl-2-stearoyl phosphatidylcholine (PSPC); 1-Stearoyl-2-palmitoyl phosphatidylcholine (SPPC); Dioleoylphosphatidylcholine (DOPC); Dilauroyloylphosphatidylglycerol (DLPG); Dimyristoylphosphatidylglycerol (DMPG); Distearoylphosphatidylglycerol (DSPG); Dioleoylphosphatidylglycerol (DOPG); Dimyristoyl phosphatidic acid (DMPA); Dipalmitoyl phosphatidic acid (DPPA); Dimyristoyl phosphatidylethanolamine (EMPE); Dipalmitoyl phosphatidylethanolamine (DPPE); Dimyristoyl phosphatidylserine (DMPS); Dipalmitoyl phosphatidylserine (DPPS); Brain phosphatidylserine (PS): Brain sphingomyelin (BSP); Dipalmitoyl sphingomyelin (DPSP); distearoyl sphingomyelin; and the like. Certain amiphiphilic compounds such as TDMAC, dihexadecyldimthyl ammonium bromide and the like can be used.

An amount of a stiffening agent can be incorporated into the liposome-forming mixture such as a suitable steroid, for example, cholesterol, ergo-sterol, coprostanol, cholestanol, cholestane and the like. Cholesterol has been suitable for such use, such as about 1 to about 40 percent, based on the weight of liposome-forming mixture.

A suitable amount of the phospholipid or other liposome-forming compound is dissolved in such solvent and the solution is placed into a suitable reaction vessel, such as a round bottom flask. The flask or other reactor is rotated under vacuum so that the phospholipid or other compound is deposited as a thin film on the inner wall of the flask. The antioxidants are then dissolved in an aqueous solution, such as a buffered aqueous solution. The aqueous solution is selected so as to maintain the pharmaceutical in a desired state. A solution of the antioxidants is added to the flask and it is agitated using, for example, a vortex mixer, whereby there is a dispersion of the antioxidants aqueous mixture and the phospholipid used to form the liposomes. The mixture is then subjected to sonication with a suitable sonicator. The mixture is generally initially turbid but becomes relatively clear when sonication results in liposome formation.

The sonicator may be a probe-type or it may be a bath type. Frequently, it is advantageous to use a bath type if it is desired that the solvent or other contents of the reaction mixture not escape into the atmosphere.

If a phospholipid is employed, a suitable amount of the phospholipid liposome-forming material can be about one part of phospholipid to about one part of the antioxidants.

Larger amounts of the liposomes can be made using appropriate scale-ups. The sonication can be carried out using appropriate wattage, such as from about 5 watts to 50 watts, when a probe-type sonicator is used. The sonication is continued until small liposomes are formed, at which point the initially turbid liquid becomes almost clear. The length of time for carrying out this reaction varies with the intensity of the sonication and other factors. Normally the reaction requires a substantial period of time such as from about 30 to 60 minutes or more. Normally, the sonication can be carried out at generally ambient temperatures or another temperature which is somewhat lower or higher without substantially interfering with the formation of the liposomes, provided that the temperature used is above the transition temperature of the lipid employed.

The liposomes can be of a moderate size and/or are of a unilamellar configuration. However, at times it is desirable to have am ultilamellar configuration. Generally speaking, it is preferred to use liposomes having a small size, less than 100 nanometers in diameter, desirably about 25 to about 75 nanometers in diameter. However, the size can be increased or decreased somewhat and still be effective and at times such smaller or larger liposomes can be desirable or preferable.

Liposomes having a size under 100 nanometers are considered in the art to be small unilamellar liposomes. On the other hand, liposomes having a size greater than 100 nanometers are considered to be large (large unilamellar liposomes). The present invention includes both types.

Multilamellar liposomes can be made as by using vortexing alone or by using a reduced degree of sonication. There are also other methods known to the art.

EXAMPLE A

Preparation of Stabilized Liposomes Containing Antioxidants

An amount of 20 mg phosphatidyl serine is dissolved in 2 ml chloroform/methanol (2:1 by volume). This solution is placed into a 50-ml flask and evaporated to dryness in a rotary evaporator under vacuum provided by a water aspirator. The resulting thin film of lipid deposited on the wall of the flask is freed of residual solvent traces by placing it under high vacuum provided by a mechanical pump for one hour. Two ml aqueous 5 millimolar Tris buffer solution at pH 7.5, and containing antioxidants are added to the flask containing the dried lipid film. The flask and contents are agitated for about one minute on a Vortex mixer to detach the lipid from the glass wall and suspending it in the solution which at this point is milky in appearance. The resulting suspension is transferred to a test tube, about 15 mm diameter and 80 mm long, with a rounded or conical end, and is sonicated with probe-type sonicator fitted with a microtip (Branson Model 140W, Heat Systems-Ultrasonics Inc.) at 30 watts, for about 45 minutes. During sonication the tube is surrounded by a water bath to maintain the temperature between 25 and 30° C. At the end of the sonication step the solution is almost clear and slightly opalescent. It now contains liposomes of about 30 to 50 nanometers in size, which are mostly unilamellar. The antioxidants are now present in the inner compartments of the liposomes.

EXAMPLE B

Preparation of Stabilized Liposomes Containing Antioxidants

The following illustrates encapsulation of amphiphilic or lipid-soluble antioxidants, as alternative to the encapsulation of water-soluble antioxidants as in Example A.

Twenty mg of PS (or other lipid or lipid mixture) are dissolved in 2 ml of methanol or chloroform/methanol (2:1), together with amphiphilic antioxidants. The solution is evaporated to dryness on a rotary evaporator under vacuum supplied by a water aspirator, then freed of residual solvent under high vacuum. Two ml of an aqueous buffer solution, 5 millimolar in TRIS or other buffer, at pH 7.5, are added. The rest of the procedure is as in Example A. The resulting liposomes now contain the antioxidants embedded in the lipid bilayer shells.

Dosages (g/kg for intravenous, aerosol, lavage, topical (e.g., optical) usages):

| | |
|---|---|
| Vitamin E | 0.001–10 g/kg |
| | 0.01–1 g/k |
| | 0.1–1 g/k |
| Vitamin C | 0.001–2 g/kg |
| | 0.01–1 g/kg |
| | 0.1–1 g/kg |
| Beta carotene | 0.0005–5 g/kg |
| | 0.005–1 g/kg |
| | 0.05–1 g/kg |
| Glutathione | 0.001–2 g/kg |
| | 0.01–1 g/kg |
| | 0.1–1 g/kg |
| Trace metals | 1–1000 µg/day |
| | 10–100 µg/day |
| Niacin (or the salt niacinamide) | 1–1000 mg/day |
| | 10–100 mg/day |

Trace metals could include 55–250 µg/day of selenium; 10–1000 µg/day of chromium; 4–40 µg/day of manganese; 2–20 µg/day of copper; 5–75 µg/day of zinc; and mixtures thereof.

Dosages (g or kg/m$^2$ for topical use on skin (e.g., burns)):

| | |
|---|---|
| Vitamin E | 1 g/m$^2$–1 kg/m$^2$ |
| | 50 g/m$^2$–500 g/m$^2$ |
| Vitamin C | 1 g/m$^2$–2 kg/m$^2$ |
| | 10 g/m$^2$–1 kg/m$^2$ |
| | 100 g/m$^2$–500 g/m$^2$ |
| Beta carotene | 1 g/m$^2$–1 kg/m$^2$ |
| | 10 g/m$^2$–500 g/m$^2$ |
| Glutathione | 1 g/m$^2$–2 kg/m$^2$ |
| | 10 g/m$^2$–1 kg/m$^2$ |
| | 100 g/m$^2$–500 g/m$^2$ |
| Trace metals | 1–1000 µg/day |
| | 10–100 µg/day |
| Niacin (or the salt niacinamide) | 1–1000 mg/day |
| | 10–100 mg/day |

Trace metals could include 55–250 µg/day of selenium; 10–1000 µg/day of chromium; 4–40 µg/day of manganese; 2–20 µg/day of copper; 5–75 µg/day of zinc; and mixtures thereof.

Routes of Administration-Liposomes with entrapped antioxidants can be administered by the following routes:

Intravenous: Venous blood passes through capillaries, to veins, to the lungs and finally the heart. Once the blood passes through the heart it becomes arterial blood. Presumably liposomes that are smaller then red blood cells will pass through the pulmonary vasculature (as do red blood cells) and eventually be distributed to the general circulation. If the liposomes are sequestered by capillary lining cells then it can be expected that a lesser concentration of the liposomes would reach the general circulation. Liposomes larger than erythrocytes would be expected to aggregate at the pulmonary system. Conventional aqueous based vehicles which are used in present day systems (e.g., hyperalimentation, normal saline, lactated ringers) can be utilized.

Intraarterial: By the intraarterial route it would be expected that on the first pass of the liposomes through the circulatory system that the pulmonary vasculature would be bypassed. Conventional aqueous based vehicles which are used in present day systems (e.g., hyperalimentation, normal saline, lactated ringers) can be utilized.

Intraperitoneal: This method of administration is frequently performed in animal experiments. It is not usually employed in humans, although it has been used in cases of ovarian cancers. Liposomes introduced by intraperitoneal injection into the intraperitoneal cavity most likely are absorbed by the capillary network in the peritoneum, and subsequently drain into the lymphatics and thoracic duct. At this point in time it is unknown whether liposomes introduced into the intraperitoneal cavity reach the general circulation, although teleologically it could be speculated that they would. Conventional aqueous based vehicles which are used in present day systems (e.g., hyperalimentation, normal saline, lactated ringers) can be utilized.

Subcutaneous, intramuscular, footpad, lymphatic system: Injections into these areas would result in the slow release of the liposomes into the general circulation and/or the lymphatics. Injections into the footpad (exclusively animal studies) show an accumulation of liposomes in the area which are drained by the lymphatics. Conventional aqueous based vehicles which are used in present day systems (e.g., hyperalimentation, normal saline, lactated ringers) can be utilized.

Intraarticular: Injection of liposomes directly into the intraarticular space. The liposomes are confined to the joint space and subsequent release of drug locally. Conventional aqueous based vehicles which are used in present day systems (e.g., hyperalimentation, normal saline, lactated ringers) can be utilized.

Intracerebrally: Due to the presence of the blood brain barrier, systemic administration of liposomes enters the central nervous system very slowly. In order to increase the concentration of liposome entrapped drugs within the central nervous system, they can be injected intracerebellarly. Conventional aqueous based vehicles which are used in present day systems (e.g., hyperalimentation, normal saline, lactated ringers) can be utilized.

Oral: There have been a few studies which have shown efficacy in the oral administration of liposome-entrapped drugs, but conversely there are reports which indicate that liposomes are completely degraded by the detergent action of bile salts. Therefore this route of administration is controversial. Conventional aqueous based vehicles which are used in present day systems (e.g., soft drinks, nutritional drinks for supplementation) can be utilized.

Topical: Applying the liposome-entrapped drug on the skin (e.g., aqueous based: gels, creams, sprays ointments), eyes (e.g., aqueous based ophthalmic ointments, saline solutions).

Aerosol: The placement of the liposomes in a vehicle or propellant which is used for administration. Conventional aqueous based vehicles which are used in present day systems (e.g., normal saline, bronchodilator medicants) can be utilized.

Intrabronchial: Direct injection of liposomes into the bronchial tree. Conventional aqueous based vehicles which are used in present day systems can be utilized.

The liposomes of this invention may contain the active compounds together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solution and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" By E. W. Martin. Such compositions will contain an effective therapeutic amount of the active compounds together with a suitable amount of carrier so as to provide the form for proper administration to the host. While intravenous injection is a very effective form of administration, other modes can be employed, as described above.

The present liposomes can be contained in conventional pharmacological forms of administration; U.S. Pat. Nos. 4,987,122 and 4,847,297 are incorporated by reference in their entirety.

The type of oxidants which are created in the in vivo microenvironment are the most important consideration in determining how they should be ameliorated. The prior art has not considered the wide range of oxidants which can be generated in biological systems, thus no method has been disclosed which would ameliorate all of the possible oxidants which occur in biological systems.

Prior to the present invention there was not method devised wherein both fat soluble, water soluble, trace minerals and niacin could be utilized. An example of the prior art belief that an antioxidant, such as vitamin E, has been incompatible in its delivery via an aqueous solution (in an effort to increase tissue levels) has been the exclusive use of vitamin E acetate in an aqueous solutions. The acetate allows alpha-tocopherol to be soluble in solution. There are no known prior examples of vitamin E in liposomes use to increase tissue levels. There are no prior examples of beta carotene being able to be solubilized in an aqueous medium (in its native form) wherein tissue levels have been increased. There are no known examples of two fat soluble antioxidants (i.e., not as the salt but in the native form) being delivered by an aqueous medium in order to increase tissue levels. There are no prior examples of niacin or trace minerals being placed in liposomes or to increase tissue levels by this vehicle.

Thus far it has been a foregone conclusion in the prior art that two types of fat soluble antioxidants could not be solubilized in an aqueous medium with one or more water soluble antioxidants. In all known experimental studies using animal models, vitamin E levels or beta carotene levels are usually increased by dietary intake or peritoneal injections. On rare occasions vitamin E levels were increased intravenously by use of the acetate (which would imply that there were no other methods of increasing vitamin E in an aqueous solution, and subsequently in tissues).

Prior to the present composition it was inconceivable to deliver native form amphipathic antioxidants (i.e. glutathione, ascorbic acid, alpha tocopherol, beta carotene, niacin, and trace minerals). The very nature of the opposite polarities of these water soluble and fat soluble substances would lead one to think they are incompatible in the same medium.

The following is a discussion of how the present invention can be used to treat various physiological states:

CYTOKINES

It is postulated that in conditions where there is excessive free radical production (e.g. AIDS), there is a severe alteration of interleukin-2 (IL-2) production which secondarily occurs due to glutathione (GSH) depletion. Excessive free radical production by an agent would appear to result on amplified production of TNF- and IL-6.

IL-2 is a glycoprotein which is produced in response to mitogens and antigenic stimuli; it and other cytokines show a multiplicity of functions (see FIG. 12). The alpha chain, the larger of the two IL-2 receptors, is regulated by glutathione levels (Baltimore). Decreasing GSH levels would decrease the affinity of IL-2 to its corresponding receptors, consequently there would be a compromise in the function of IL-2. It is postulated that maintenance of GSH levels by the use of amphiphathic liposomes would allow IL-2 and its receptors to elicit the normal immunological response for this particular interleukin.

Figure 14:
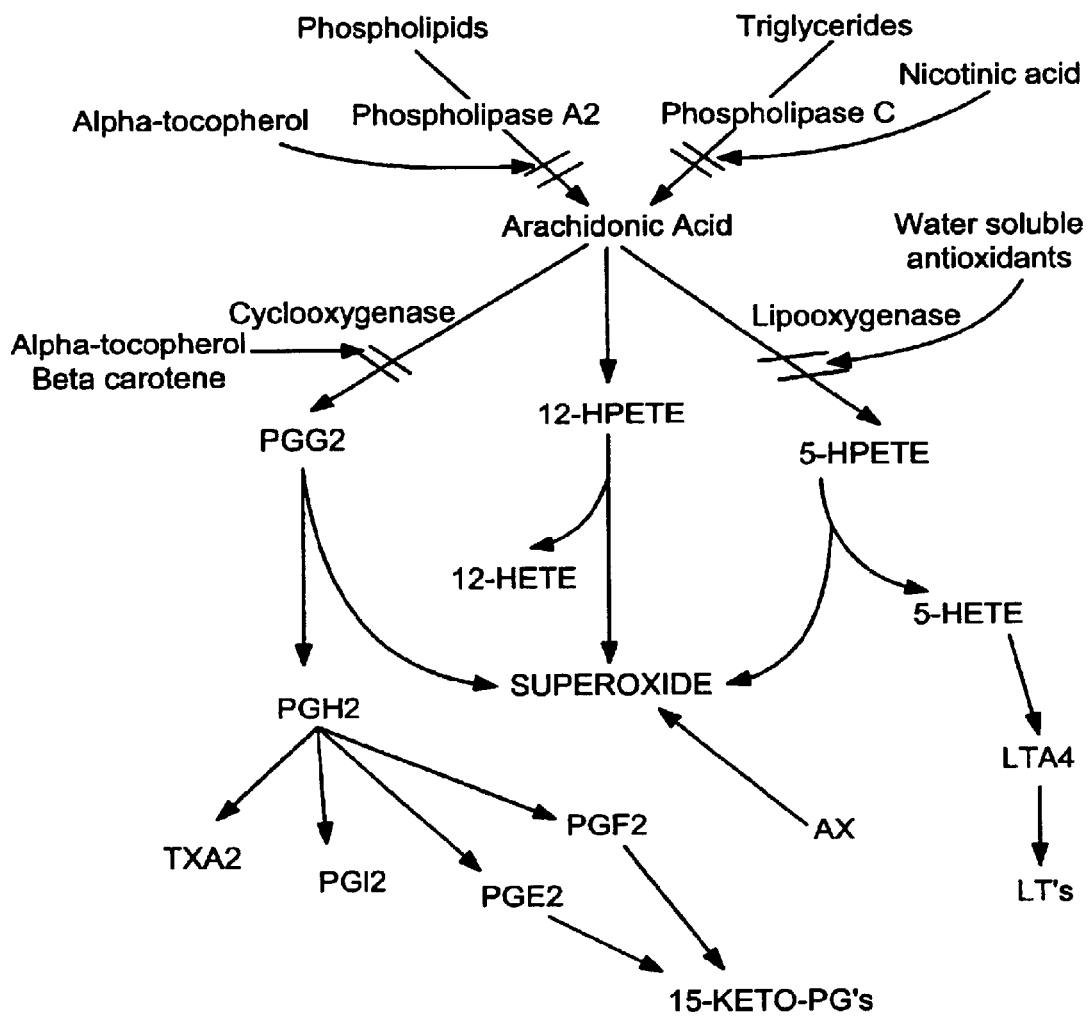
FIG. 14—arachidonic acid metabolism and enzymatic inhibitors.
Figure 15:
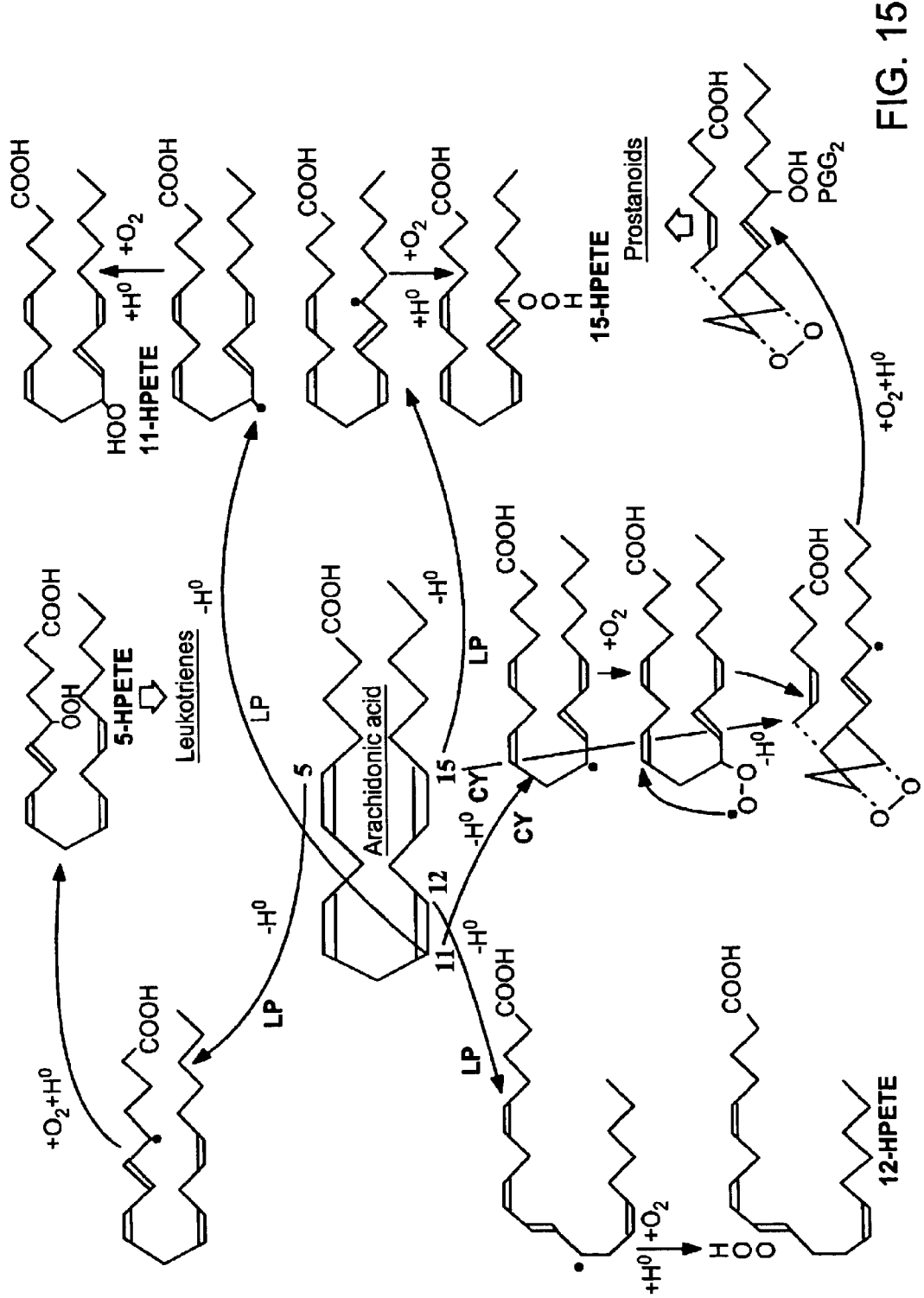
FIG. 15—prostaglandin metabolite intermediates.
Figure 17:
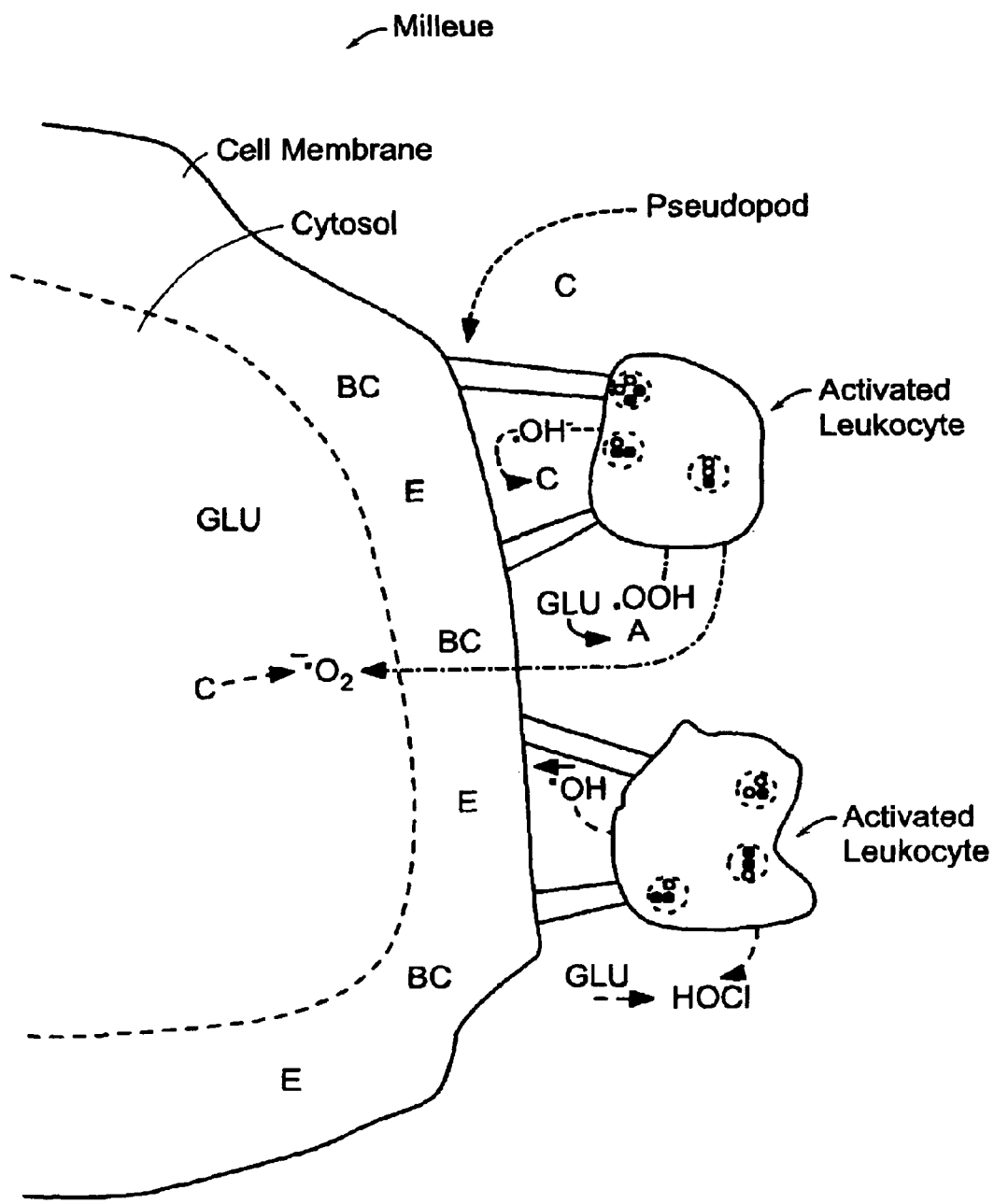
FIG. 17—oxidant interaction with liposomes.

Production of tumor necrosis factor-alpha (TNF-α) by macrophages is stimulated by free radicals or oxidants (Chaudhri, G. and Clark, I. A.: J Immunol, vol. 143, 1990–1294, No.4, 1989). TNF-α induces oxidant production by stimulating leukocytes, releasing arachidonic acid from leukocytes (see FIG. 12), and releasing lysosomes. By enhancing plasma levels of antioxidants it would be postulated that there would be a decrease in the production of TNF-α (see section on AIDS, inflammation, burns; see FIGS. 13, 14, and 15).

GELATINASE/COLLAGENASE

Collagenase and gelatinase are metalloenzymes found in their latent forms. Hypochlorous acid, generated in any inflammatory reaction, reacts with the latent forms of these two enzymes to convert them to an active form. Collagenase and gelatinase are believed to facilitate the migration of inflammatory cells into the area of the inflammatory focus. It is postulated that the enhancement of amphipathic antioxidants specific for the amelioration of hydrogen peroxide and hypochlorous would reduce the concentrations of collagenase and gelatinase which are activated.

BURNS/WOUND HEALING

Burn wounds to skin and other organs can occur by ultraviolet radiation (uv), chemical agents, conductive or convective heat, electrocution, etc. Burns can occur in lung parenchyma by the inhalation of smoke or caustic gases (see section on tissue injury). Burn wounds to the skin are graded as first, second, and third degree burns (the most severe). It is postulated that any burn wound produces tissue damage, largely by the production of oxidants (Till, G. O.: Am J. Pathol., Jul; 1325(1): 195–202, 1989). Liposomes (artificial membranes) when exposed to uv undergo peroxidation (Bose, B: Biotechnol Appl. Biochem, Oct., 12 (5): 557–61, 1990). It has been postulated that similar peroxidation occurs in skin when it is exposed to uv radiation (Somer, E.:Shape Magazine, p 33–35, Nov. 1992; Hamanka, H.: J. Dermatol, Oct. 17(10):595–8, 1990). Exposure of skin to uv varies in intensity and length of exposure. Daily exposure to uv (e.g., sunlight) has been postulated to result in skin wrinkling. Depending on the intensity and/or length of skin exposure to uv light, first, second or third degree burns can result.

Hairless mice exposed to a single exposure of uv resulted in a broad range decrease of antioxidants: glutathione, beta-carotene, alpha-tocopherol. The enzyme activity of catalase and glutathione reductase were also decrease (Fuchs, J.: J. Invest Dermatol, Dec., 93(6): 769–73, 1989). These decreases in the concentration of antioxidants and enzyme activity in skin due to uv exposure supports the concept of the occurrence of free radicals in skin. It is postulated that lipid peroxidation could be inhibited by an enhancement of amphipathic antioxidants in skin. Lipid peroxidation in liposomes exposed to uv can be inhibited by placement of beta-carotene or alpha-tocopherol in liposomes (Pelle, E.: Arch. Biochem. Biophys. Dec. 283 (2): 234–40, 1990). It is postulated that increasing amphipathic antioxidants in skin would also inhibit lipid- peroxidation in skin (Bissett, D. L., et al.: Photodermatol Photoimmunol Photmed, Apr:, 7(2): 56–62, 1990).

In experimentally produced severe burns, remote organ injury is observed (e.g. microvascular injury). It is postulated that it is the activation of leukocytes, the production of cytokines, and the pathological production of prostaglandins which are responsible for the damage seen in burn wounds (see section on inflammation, tissue injury, collagenase/gelatinase, see FIGS. 12, 13, and 14). Excessive free radical production has been cited as a factor in delayed wound healing (Yukie, N.: Dermatolgica, 179 (suppl 1): 101–106, 1989). Topical, aerosol, or intravenous administration of antioxidants would ameliorate the effects of pathologic oxidants and prostaglandin production as well as promote wound healing in various skin injuries.

TISSUE INJURY

Figure 5:
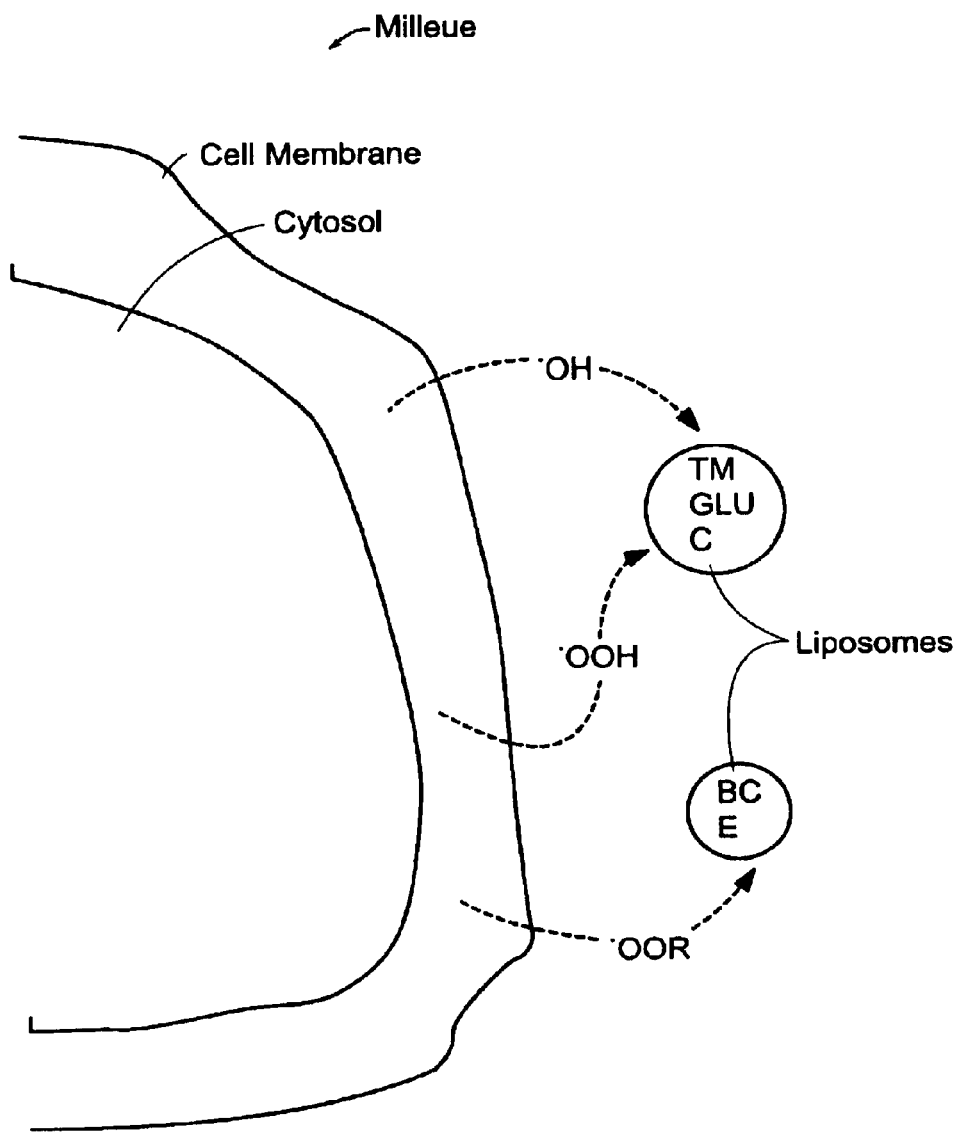
FIG. 5—oxidant interaction with liposomes.
Figure 6:
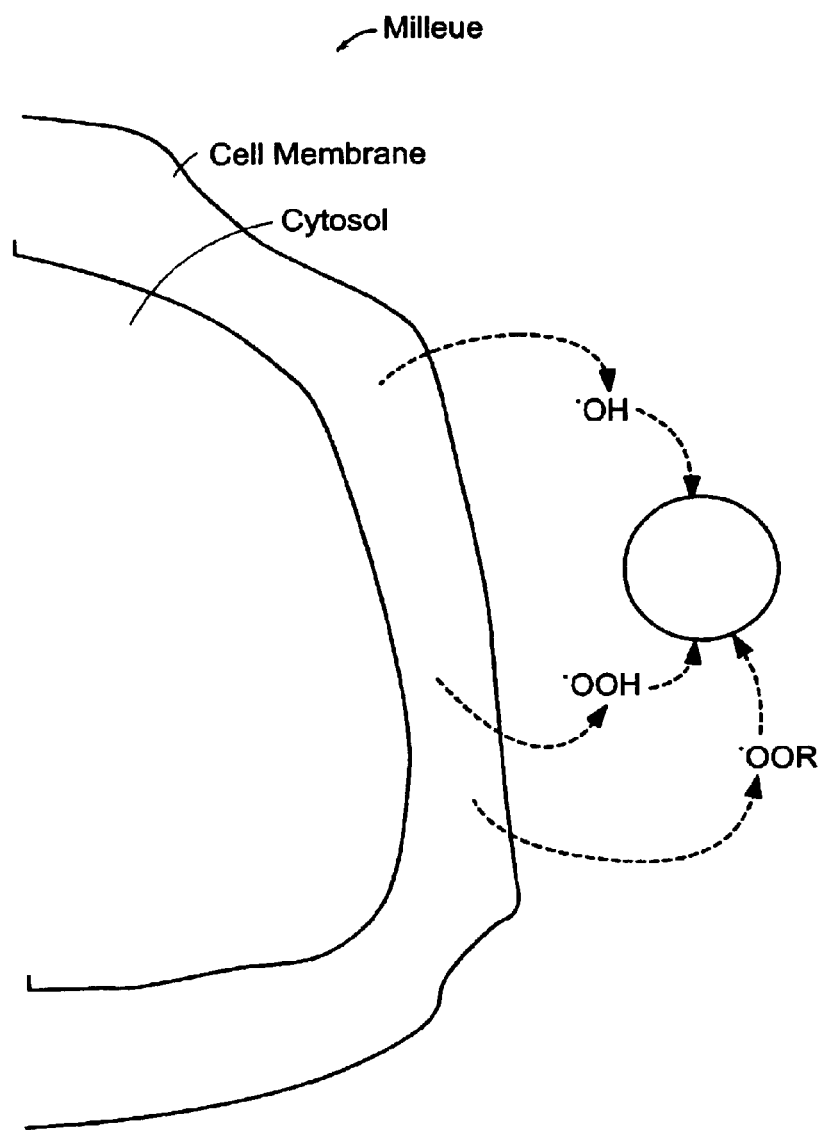
FIG. 6—oxidant interaction with liposomes.
Figure 7:
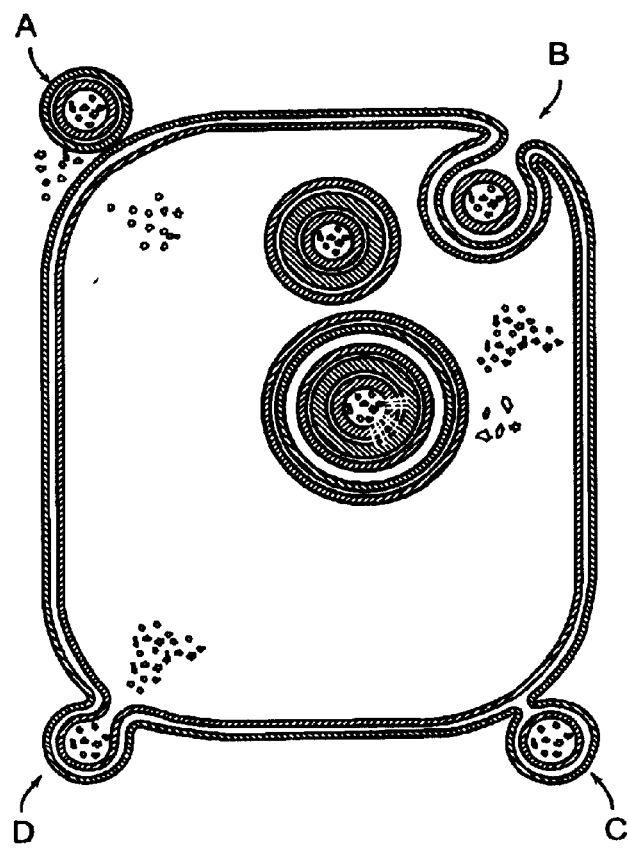
FIG. 7—liposome cellular interaction.
Figure 8:
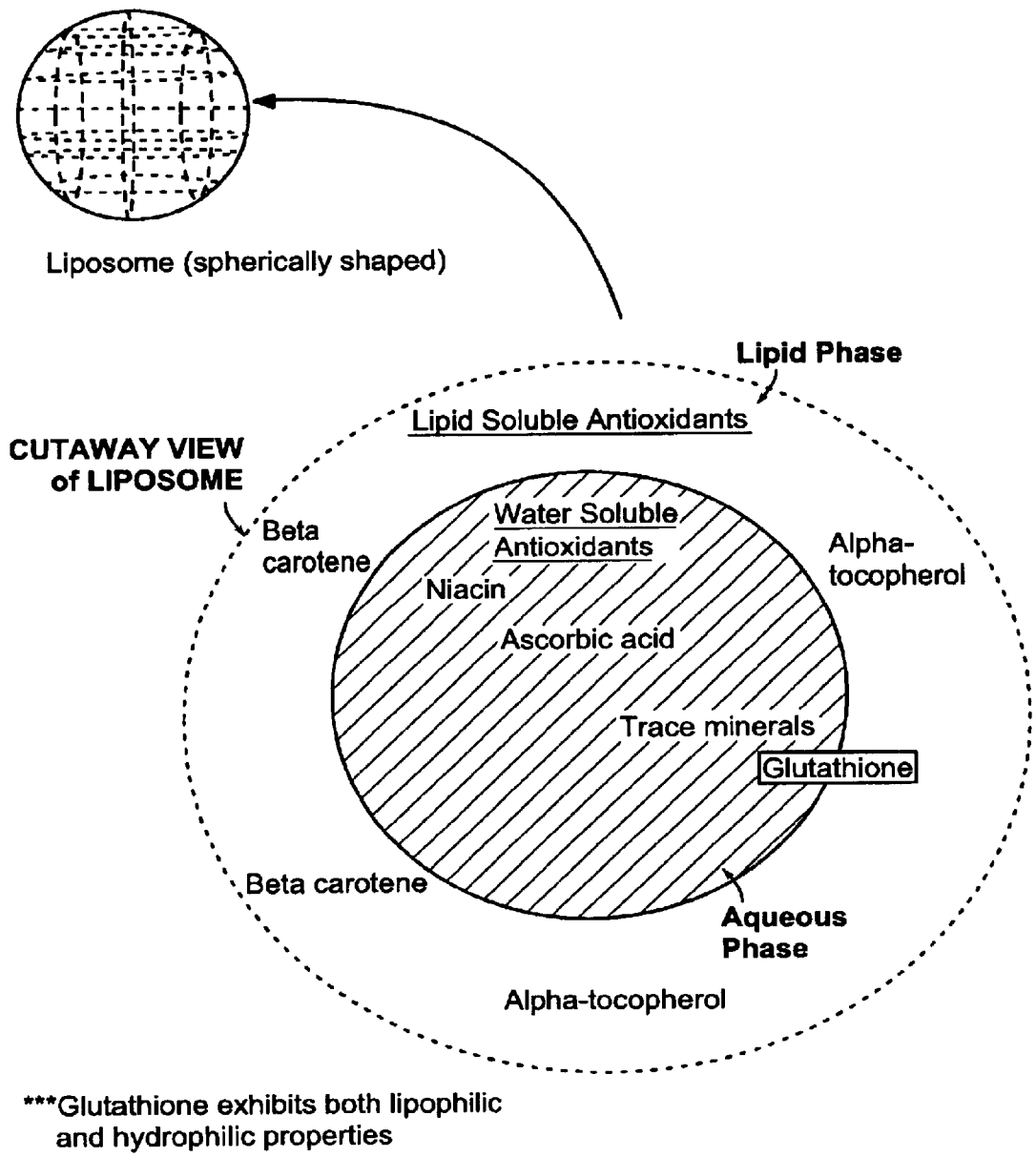
FIG. 8—an example of an amphipathic antioxidant composition.
Figure 9:
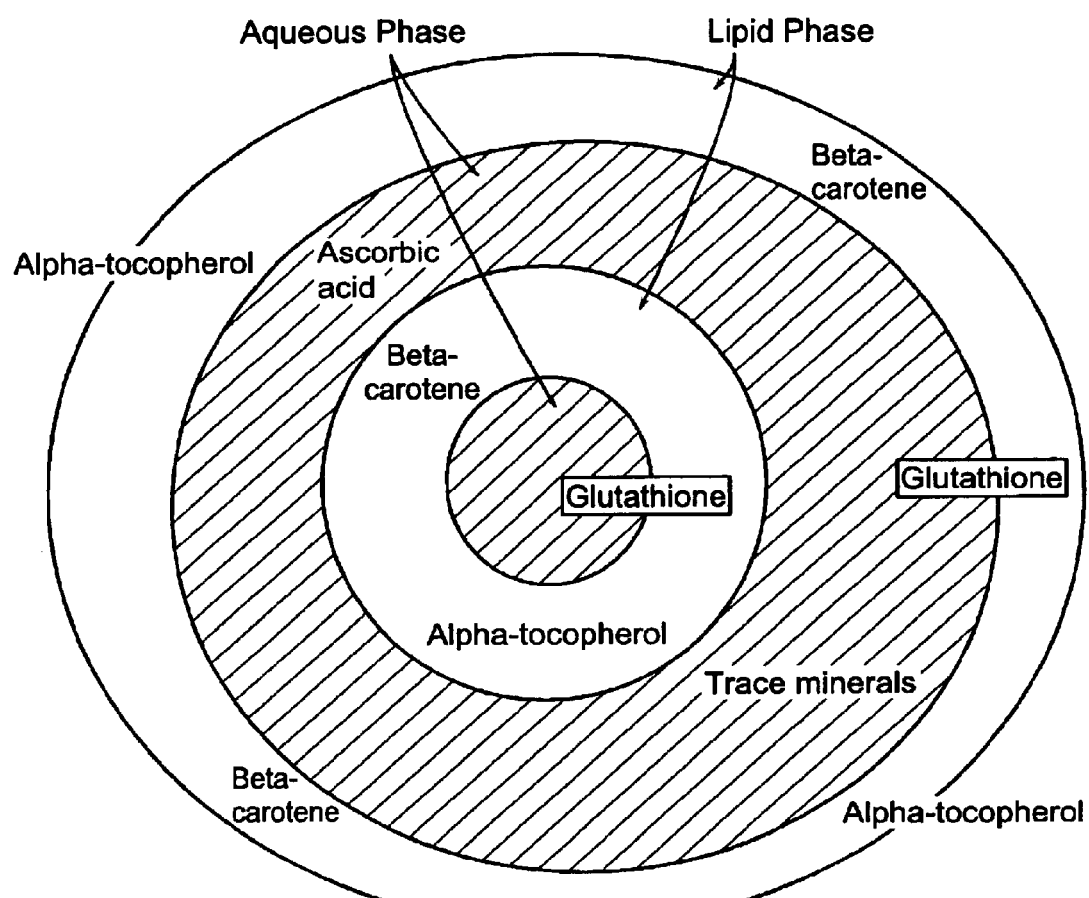
FIG. 9—multilamellar amphipathic liposome.
Figure 10:
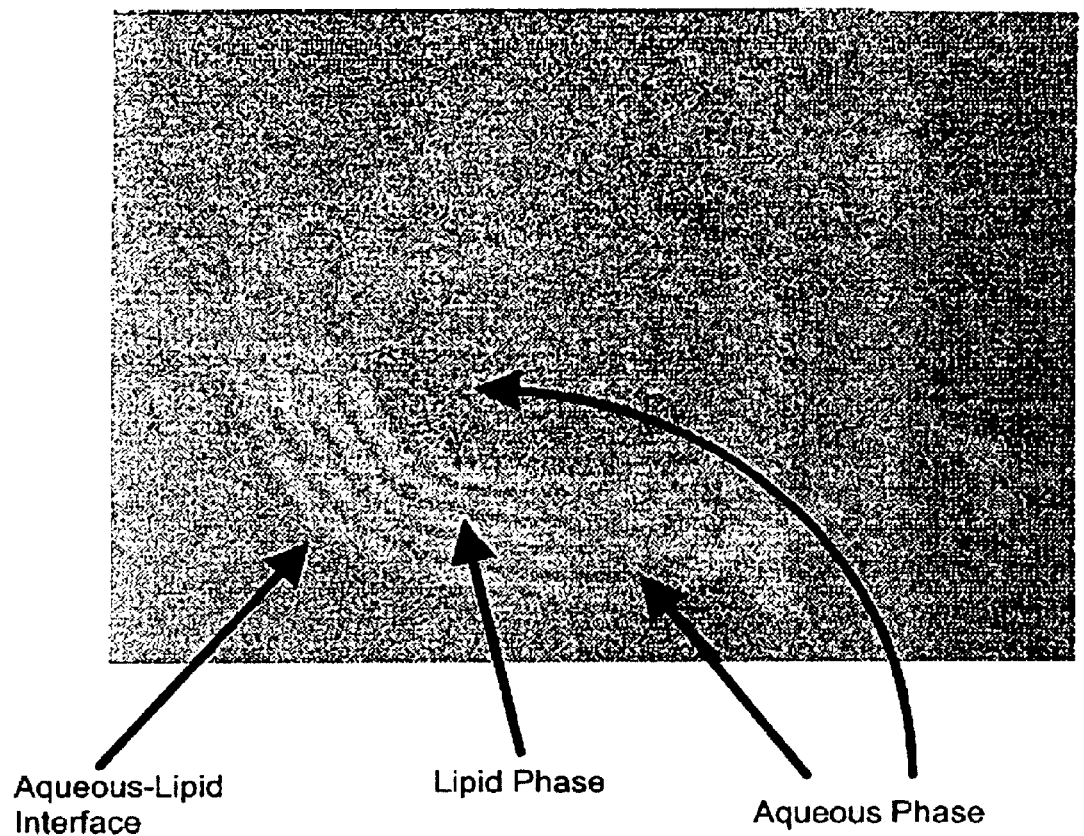
FIG. 10—electron micrograph of a multilamellar liposome.
Figure 11:
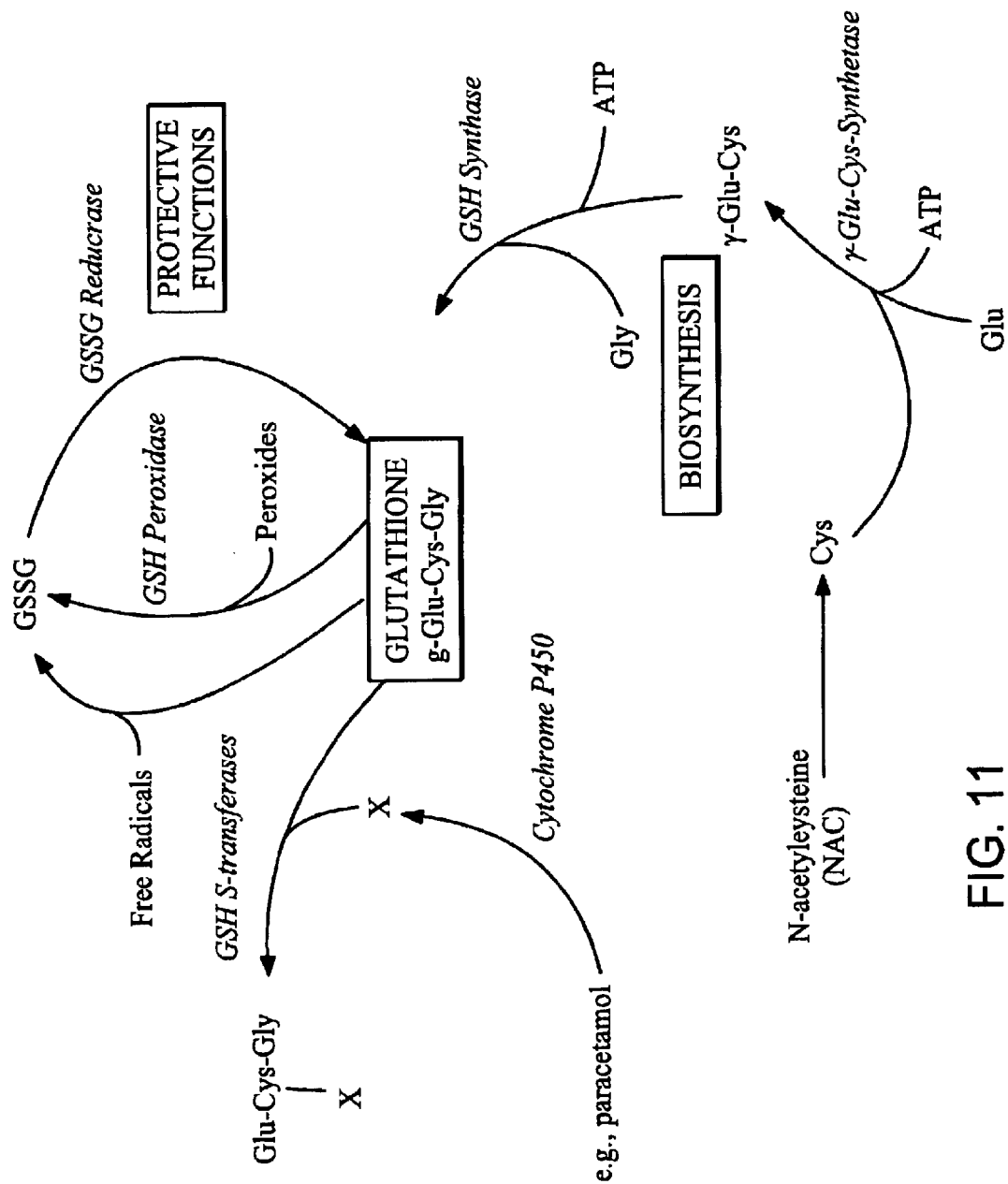
FIG. 11—glutathione metabolism.

Tissue injury occurs as a result of an inflammatory focus occurring in the area of a cell or an organ. Inflammation can occur due to a local inducement (e.g. hepatitis) or due to an injury occurring to one organ in a remote location and another discontiguous organ which also sustains an injury (e.g., severe burns occurring to skin (the first organ) with subsequent injury to the lungs (the second organ)). In either case, local or remote tissue injury is believed to be mediated by activated leukocytes which release oxidants. Oxidants released from leukocytes react with cellular (organ) membranes (Fantone,. J. C. and Ward, P. A.: Am. J. of Path., vol. 107(3), P. 397–418, 1982). Repeated cellular membrane exposure to oxidants decreases antioxidant levels, which increases their susceptibility to damage. Increasing the levels of amphipathic antioxidants in the extracellular and/or intracellular, and/or the lipid-aqueous interface (see FIGS. 5, 6), is postulated to thwart oxidant damage to vital cellular structures.

SEPSIS

Sepsis is characterized as a systemic infection by a microorganism. Frequently it is fatal and if not fatal increases the morbidity of the patient. In sepsis, red blood cells become sticky and deformed (Baker, C. H., et al.: Circ. Shock 20:127–139, 1986; Powell, J., et al.: Critical Care Med., vol 19 (5), 1991), which can lead to occlusion of the microvasculature. Cardiac output is increased, but in the kidney, liver, and musculature blood flow is decreased (Hurd, T. C., et al.: Archives of Surg., vol. 123, 1988). Evidence of free radical damage has been demonstrated in in vitro and in vivo studies involving shock induced by endotoxins (McKechnie, K., et al.: Circ. Shock 19: 429–439, 1986). Findings include increased vascular permeability, damaged mitochondria, disruption of calcium transport by the sarcoplasmic reticulum, and the activation of the complement system (particularly C5a (see FIG. 13)). The antioxidants vitamin E and PBN (phenyltertylnitrone, an intracellular spin trapping agent) in separate experimental protocols were found to result in mortalities of 46% and 42% respectively. This was in comparison to controls (which were glutathione or SOD) which showed a 100% mortality. In the present composition, extracellular fat soluble antioxidants (alpha-tocopherol and beta- carotene) can be increased. Intracellular antioxidants can be increased in order to quench intracellular free radicals.

GSH DEFICIENCY

Artificial depletion of glutathione interferes with normal T cell function, particularly within the first 30–60 minutes of activation (Fischman, C. M., et. al: The Journal of Immunology, vol. 127(6), p2257–2262, 1981; Hamilos, D. L. and Wedner, H. H.: The Journal of Immunology, vol. 135 (4), 1985). Glutathione deficient T cells showed a decrease in thymidine incorporation and blast transformation. The greater the depletion of glutathione the longer it took cells to recover to normal levels. If cellular GSH depletion was severe enough the cells never recovered to normal GSH levels. Increased glutamate levels, which are found in AIDS patients (Eck, H.-P. and Droge, W.: Bio. Chem. Hoppe-Seyler, vol. 370, pp 109–113), appear to inhibit the transport of cystine into macrophages. Under normal circumstances cystine is reduced to cysteine by the macrophages. Cysteine is exported into the microenvironment for the use of T cells for the ultimate conversion to intracellular glutathione. T cells can not utilize cystine. In AIDS patients glutathione is depleted (Eck, H.-P, et al.: Biol. Chem. Hoppe-Seyler, vol. 370, pp101–108), which is postulated to adversely effect T cell function. This scenario is believed to be similar to the experimental studies which demonstrated abnormal T cell function as a result of artificial GSH depletion. It is postulated that GSH deficiency could be corrected by the use of the present invention, by liposomal interaction with bone narrow cells, T lymphocytes and by plasma increases in amphipathic antioxidants in general.

AIDS

There is considerable evidence which indicates that HIV infection and subsequently ARC/AIDS is by in large a free radically mediated disease. This analysis can be made indirectly as judged by the antioxidant levels in humans and their consequences on the immune system. On of those antioxidants, glutathione (GSH), is decreased as a result of HIV infecting the host. The GSH levels continue to decrease as the disease progresses through ARC and finally to AIDS. Micromolar changes in GSH levels have an untoward effect on the function of T lymphocytes (which can be viewed as the pivotal leader of the immune system). GSH shows a multiplicity of uses in the immune system (see FIG. 12). Thiol concentrations (e.g. GSH) regulate the replication of HIV genomic expression (Kalebic, T., et al.: Proc. Natl. Acad. Sci., USA,; 88: 986–90, 1991; Roeder, M., et al.,: Porc. Natl. Acad. Sci., USA, vol. 87, p 4884–4888). Increasing the concentrations of thiols (GSH, NAC, GSE (glutathione ester)) in culture medium of U1 cell line (promonocytes) results in suppression of viral assembly, HIV reverse transcriptase production and viral replication. It is postulated that the present composition of amphipathic antioxidants would increase and maintain the intracellular concentration of GSH. GSH levels could be maximally enhanced on a consistent basis by intravenous infusions of amphipathic liposomes. In addition, all of the normal cellular functions which are normally dependent upon normal GSH levels would once again establish normalcy in function.

IMMUNOMODULATION

There are numerous activators of leukocytes (e.g., exposure to ingestible particles, certain soluble factors such as complement, lectins, phorbol esters, etc.). A consequence of leukocyte activation is the release of the MPO system ($H_2O_2$+halide+myleoperoxidase) and other oxidants. The more potent the stimulus of activation of leukocytes, the greater the release of oxidants and the greater the suppression of T lymphocytic function. When activated leukocytes were combined with T lymphocytes and catalase, there was no suppression of lymphocytic function; monocytes (which contain enzymatic antioxidants: glutathione peroxidase, catalase, myeloperoxidase) were used in lieu of catalase, again there was no suppression (Lipsky, P. E.: J. Clin, Invest. 73:53, 1984). Antibody production by B lymphocytes showed a similar susceptibility to free radical damage as did lymphocytes (El-Hag, A., et al.: J. of Immunol., vol. 136 (9), 1986). A following is a rank order for various lymphocytic functions to free radical attack: immunoglobulin secreting cells were the most sensitive (particularly to the MPO system); Natural Killer cell activity, DNA synthetic responses to PHA and Con A were intermediate; and the DNA response to PWM was the least susceptible. Monocytes/macrophages have approximately 15–20 times higher catalase content in comparison to lymphocytes (Meerhof, L. J. and Roos, D.: J. Reticulendothel. Soc. 28: 419) and would therefore be much less susceptible to oxidative damage. Lymphocytes exposed to a free radical generating system demonstrate changes in membrane characteristics: 63% decrease in E rosette formation, 44% decrease in surface immunoglobulins and 90% decrease in cap formation (Kraut, E. H. and Sagone, A. L.: J. of Lab. Clin. Med., Nov. 1981, p 697–703). Amphipathic antioxidants can be used in lieu of catalase or monocytes (which also contains enzymatic antioxidants) since oxidants which are quenched by either catalase or the enzymes contained in monocytes are the same oxidants which will be reduced by the amphipathic antioxidants.

INFLAMMATION

Inflammation can arise from infective agents (e.g. virion), trauma, chemical agents, immune reactions, metallic agents, ionizing or thermal agents. The sine qua non of inflammation are heat, redness, edema pain and loss of function (e.g., of the surrounding tissue). In any type of inflammation, characteristic inflammatory cells can be found, for example leukocytes, eosinophils, macrophages/macrocytes. Each of these cell types produce free radicals as part of a programmed response. Also as part of that "programmed" response are the production of cytokines, such as TNF-α, CM-CSF and IL-6. These particular cytokines promote the production of oxidants. Oxidants are also generated as a byproduct of prostaglandin production, which is part of the propagation and amplification of the inflammatory process. Platelets are also involved in the inflammatory process by virtue of their ability to act as a plug (as in a clot); but also due to their liberation of platelet activating factor (PAF). PAF liberates arachidonic acid from leukocytes (see FIGS. 13, 14).

The production of prostaglandins is dependent upon the free radical tone (or concentration) of the microenvironment and metabolite synthesis. By decreasing the free radical tone and PG free radical intermediate metabolites, it is postulated that the pathological production of prostaglandins would be reduced (see FIGS. 14 and 15), the amplification effect that PGs have as a role in the inflammatory process could be limited. Theoretically, either the lipooxygenase limb or the cyclooxygenase limb of the prostaglandin pathway could be effected by an increased ratio of water soluble antioxidants to fat soluble antioxidants, or fat soluble antioxidants to water soluble antioxidants.

Free radicals or oxidants also have a plethora of different effects on the tissue in which it occurs, e.g. membrane damage, platelet adhesion, blood vessel intimal damage, etc. By artificially increasing the antioxidant levels in areas where inflammation is occurring, it is postulated that the propagatory effect, tissue damage and pathologic physiologic reactions would be curtailed as well (see FIGS. 2, 11, 13, 14, 15). The NF-KB transcription protein regulates the expression of a number of genes for proteins and cytokines involved in the inflammatory process (Baeuerle, P. A. and Baltimore, D.: Science, vol. 242, Oct, 1988). The activity and affinity that the NF-KB protein has for DNA is also regulated by GSH level (Staal, F. J. T, et. al.: Proc. Natl. Acad. Sci., USA, vol. 87, pp 9943–9947, Dec. 1990; Duh, E. J., et. al.: Proc. Ntal. Sci. Acad., USA, vol. 86, p 5974–5978, 1989). Enhancing levels of GSH decreases the activity and binding of NF-KB to DNA. It is postulated that by enhancing GSH levels that those cytokines and proteins involved in the inflammatory process would be decreased.

Figure 13:
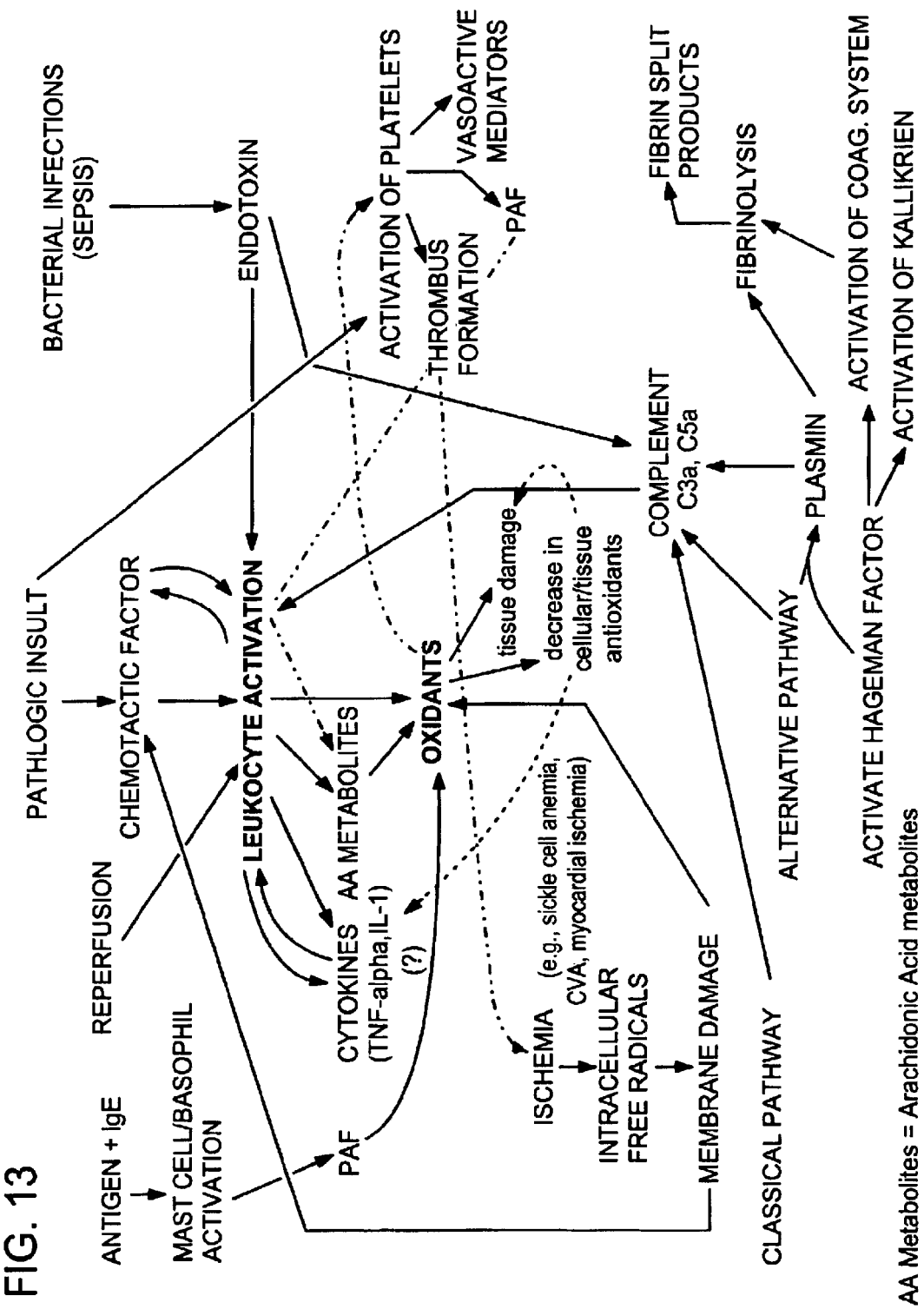
FIG. 13—theoretical pathway of pathologic oxidant production.

ISCHEMIA AND REPERFUSION (see FIG. 13)

Ischemia, which is low tissue oxygen saturation of a given tissue, can occur in any organ system. All organs require a blood supply in order to remain viable. The intact organ whose arterial supply is compromised (either by partial or total occlusion) is rendered ischemic (e.g., coronary artery occlusion, organs awaiting transplantation, cerebral vascular accident, compartment syndrome, etc.). There are reversible and irreversible histological, physiological and biochemical changes which occur as a result of ischemic injury to tissue. End stage ischemia is universal and demonstrates necrosis. Demopoulos et. al. (Fed. Proc. 32:1859–1861, 1973b) theorized that the necrosis observed in ischemic tissue was due to oxidants generated by the uncoupling of the oxidative phosphorylation chain in mitochondria. Direct evidence of free radical production as a result of ischemia was provided by Zweir et al. (Proc. Natl. Acad. Sci. USA, vol. 84, pp: 1404–1407) by the use of electron spin resonance spectroscopy. In reperfusion studies Zweir was able to show the alteration of one of the free radicals with the use of superoxide dismutase (which eliminated superoxide). In ischemic cardiac myocyte a depletion of ATP induces the release of arachidonic acid (see FIGS. 14,15) and palmitic acid. Vitamin E (Massey, K. D. and Burton, K. P.: Am. J. Physiol. 256 (Heart Circ. Physiol. 25): H1192–H1199, 1989), vitamin E acetate and selenium selenite have been used to protect tissue against free radicals which have occurred in ischemia. It is postulated that enhancement of tissue amphipathic antioxidants would eliminate the superoxide free radical, as well as other oxidants that are not double produced as a result of ischemia and prostaglandin metabolite production; vitamin E would tend to inhibit the activity of phospholipase A2, whereas niacin would tend to inhibit the function of phospholipase C (see FIG. 14).

SICKLE CELL ANEMIA

Sickle cell anemia is a genetically determined disease. Analysis of sickle cell patients RBC (HbS) demonstrates a number of peculiarities of the membrane: frozen spectrin shell of irreversibly sickled RBC, an abnormal orientation of the lipid bilayer phospholipids, deficient calcium-ATPase, a propensity for HbS RBCs to adhere to vascular endothelium, and oxidized thiol groups on the HbS molecule. It is the characteristic of the tendency of adherence to the vascular endothelium which is the likely primary pathogenesis of the disease, which is vasoocclusion of the microvasculature. Consequently, ischemic injury occurs to organs (see section on ischemia, see FIG. 13). Additional evidence of free radical damage to HbS are a deficiency of alpha-tocopherol, increased amounts of malondialdehyde, and abnormal group cross linking by malonadehyde. Superoxide anion can enter into erthrocytes via anion channels, resulting in the formation of methemoglobin and the ultimate lysis of erythrocytes (Weiss, S. J.: J. Biol. Chem. 225: 9912–9917, 1980). Sickle RBCs spontaneously generate sixty percent greater quantities of superoxide and approximately 75% more hydrogen peroxide when compared with controls (Hebbel, R. P., et. al.: J. Clin. Invest., vol. 70, p. 1253–1259, 1982). Superoxide dismutase is increased by about 50%, glutathione peroxidase and catalase were decreased by approximately 50 and 29% respectively. Glutathione and vitamin E levels were significantly reduced. It is postulated that by increasing both bone narrow and serum amphipathic antioxidant levels that free radicals produced by sickled RBCs would be markedly reduced. Vitamin E levels have been found to be difficult to augment by oral administration. Increasing antioxidant levels in RBCs and in plasma by intravenous administration at the time of a crisis (an ischemic event), it is postulated that RBCs would be less sticky and less prone to adhere to the microvasculature intimal lining. Given that plasma levels of amphipathic antioxidants were to remain high, it would be postulated that there would be less damage due to ischemia (e.g., decrease the extent of a cerebral vascular accident or decrease the extent of pain which is due to ischemia, etc.).

Method of diagnosing free radical damage-On the clinical level, antioxidant administration and liposome configuration will be determined by the location of the preponderance of the oxidants generated, the type of oxidants, and the generation of pathological prostaglandins (for example, as shown by the following clinical examples).

Administering AMAOX-The administration of AMAOX is dependent upon where pathological free radical reactions are taking place. AMAOX can be utilized as a method to eradicate free radical reactions presently taking place or it may be used as prophylaxis against pathological free radical reactions which may occur as a result of a possible oxidant promoting incident (e.g., ischemic injury).

Monitoring results-Monitoring the results of the effectiveness of AMAOX can be done by measuring the rate of the appearance of oxidation products. Effectiveness can also be monitored in patients by their clinical progress.

EXAMPLES

Example 1

Additive to Facial Moisturizers (refer to FIG. 13, also not Section on Burns)

Amphipathic antioxidants (AMAOX) may be added to an aqueous based moisturizer. The moisturizer may then be added to facial skin once or twice a day. This moisturizer may be also used as night cream. Since most of the lipids in skin are phospholipids, it would be expected that liposomes composed of phospholipids will be readily absorbed by cellular membranes. An increase in skin amphipathic antioxidants would be expected to decrease lipid peroxidation in the various layers of the skin. Free radicals have been implicated in the aging of facial skin due to the exposure to ultraviolet light.

| Moisturizer (10 ounces) | AMAOX | Amounts |
|---|---|---|
| | Vitamin E | 3000 mg |
| | Beta-carotene | 1500 mg |
| | Glutathione | 500 mg |
| | Vitamin C | 500 mg |

Example 2

(Refer to FIG. 13, also Note Section on Burns)

Application to Skin for Burn Wounds

Given a 25 year old male who sustains a 50% body surface burn wound. Once the burn wounds are debrided, a gel based vehicle containing AMAOX is applied to the entire surface of the areas of the burns. AMAOX is also administered for several days intravenously (twenty four hours per day). The application of AMAOX to skin which had sustained a serious burn wound would be postulated to decrease lipid peroxidation which takes place on the skin after burn wounds. Intravenous amphipathic antioxidants would maintain systemic levels of antioxidants, which is postulated to prevent or limit adult respiratory distress syndrome (which has been postulated as having free radicals as its pathogenesis), and assist in facilitating healing of the wounds.

| For Burn Wounds | AMAOX | Concentrations Intravenous Topical |
|---|---|---|
| | Vitamin E | 5 g/Kg/day |
| | | 1 Kg/M²/day |
| | Beta-carotene | 2 g/Kg/day |
| | | 1 Kg/M²/day |
| | Vitamin C | 0.5 g/Kg/day |
| | | 2 Kg/M²/day |
| | Glutathione | 0.5 g/Kg/day |
| | | 1 Kg/²/day |
| | Selenium | 5 ug/Kg/day |
| | Copper | 1 g/Kg/day |
| | Zinc | 2 mg/Kg/day |
| | Manganese | 1.3 mg/Kg/day |

**Copper, Manganese, Zinc and Selenium should only be given for two days intravenously.

Example 3

A patient with hepatitis (see FIG. 13, see Section on Inflammation)

Given a patient experiencing pain and appearing jaundiced. His liver function enzymes are elevated. Free radicals have been shown to occur in hepatitis. It is believed that free radicals occur as a part of the inflammatory process. Intravenous amphipathic antioxidants are administered in an effort to limit the tissue damage done due to free radicals. AMAOX would be postulated to decrease inflammation and facilitate resolution of the inflammation.

| For inflammation in the liver | Liposomes | AMAOX | Concentrations |
|---|---|---|---|
| Hepatitis | negatively charged to facilitate uptake by macrophages in liver | Vitamin C | .25 g/Kg/day |
| | | Glutathione | .25 g/Kg/day |
| | | Beta carotene | 0.7 g/Kg/day |
| | | Vitamin E | 0.7 g/Kg/day |

Example 4

(See FIG. 13, Refer to Section on Ischemia and Reperfusion)

Ischemia

Given a 65 year old man experiencing severe chest pain when he arrived at the hospital. He is diagnosed as having a heart attack (myocardial ischemic injury). AMAOX are administered as soon as the diagnosis of a myocardial infarction is made. This is done in an effort to decrease the pain secondary to ischemia and also the postulated damage to tissue due to the free radicals. Increasing the AMAOX levels would also protect the myocardial tissue from reperfusion injury which no doubt occurs as a result of the use of thrombolytics such as TPa or streptolysin). It is postulated that the level of antioxidants would be initially high and then be tapered off after the acute injury period.

| For cardiac ischemia | AMAOX | Concentrations Intravenous |
|---|---|---|
| | Vitamin C | 0.2 g/Kg/day |
| | Vitamin E | 0.5 g/Kg/day |
| | Beta carotene | 0.5 g/Kg/day |
| | Glutathione | 0.1 g/Kg/day |

After the first twenty four hours the dosages should be decreased by 50%, and then titrated up or down given the particular patient response.

Example 5

(See FIG. 13)

Sepsis

Given a 25 year old man who is an IV drug abuser and is diagnosed as being septic. He experiences fevers and delirium. As a complication of the sepsis he develops adult respiratory distress syndrome (ARDS). He is placed on a respirator due to progressively worsening breathing difficulties. In both sepsis and ARDS free radicals have been implicated as part of the pathogenesis. AMAOX in this case be would be administered intravenously and by aerosol. It is postulated that the morbidity of the sepsis and ARDS would be diminished with the use of AMAOX.

| For Sepsis | Liposomes | AMAOX | Concentrations Intravenous Aerosol |
|---|---|---|---|
| | Negatively charged | Vitamin C | 0.1 g/Kg/day |
| | | | 0.01 g/Kg/day |
| | Positively charged | Vitamin E | 1 g/Kg/day |
| | | | 0.01 g/Kg/day |
| | Unilamellar | Beta carotene | 1 g/Kg/day |
| | | | 0.01 g/Kg/day |
| | Multiamellar | Glutathione | 0.1 g.Kg/day |
| | | | 0.01 g/Kg/day |
| | Multivesicular | | |

Example 6

(See FIG. 13, Refer to Section on Ischemia)

Ischemia

Given a 35 year old man working on a railroad track and who falls on the tracks while a train was passing. The right leg is severed below the knee. The severed limb immediately becomes ischemic. He is taken to a large metropolitan hospital for reimplantation of the limb. AMAOX are started intravenously as soon as he arrives at the hospital. The severed limb is continuously perfused with AMAOX for approximately thirty minutes prior to reimplantation.

AMAOX in this case would decrease the postulated occurrence of free radicals which occurs as a result of a traumatic injury. It would is postulated that by maintaining AMAOX levels would healing would be facilitated. The free radicals which are known to occur in ischemia would be reduced, subsequently reducing tissue damage.

| For Ischemia | AMAOX | Concentrations |
|---|---|---|
| | Vitamin C | 0.1 g/Kg/day |
| | Vitamin E | 0.1 g/Kg/day |
| | Glutathione | 0.1 g/Kg/day |
| | Beta carotene | 0.1 g/Kg/day |

Example 7

Aids

Given a male diagnosed as having AIDS. His T4 lymphocyte count is 50. He experiences an approximately 15 kilogram weight loss. He also experiences loss of appetite, fevers and diarrhea. A chest X-ray reveals a pneumonic process, that is later diagnosed as Pnuemocytis carinii. Intravenous fluids are administered. Water soluble antioxidants are to be administered on the basis of ideal body weight composition. Fat soluble antioxidants are to be administered on the basis of ideal body fat composition. Trace minerals are administered based on the deficit of the various trace minerals.

| Intravenous amphipathic antioxidants: | |
|---|---|
| Water soluble antioxidants | |
| Vitamin C | 0.25 grams/Kg/day |
| Glutathione | 0.3 grams/Kg/day |
| Fat soluble antioxidants | |
| Vitamin E | 1 gram/Kg/day |
| Beta-carotene | 0.5 gram/Kg/day |
| Trace minerals | |
| Selenium | 0.1 ug/Kg/day |
| Copper | 1 mg/Kg/day |

| Aerosolized amphipathic antioxidants: | |
|---|---|
| Water soluble antioxidants | |
| Vitamin C | 0.05 gram/Kg/day |
| Glutathione | 0.05 gram/Kg/day |
| Fat soluble antioxidants | |
| Beta-carotene/ | 0.05 gram/Kg/day |
| Vitamin E | 0.05 gram/Kg/day |

Infusions would be given constantly 24 hours per day. The rational being that the bone narrow is continuously producing new lymphocytes, red blood cells monocytes, etc., and amphipathic antioxidants level would be already boosted in the new bone marrow cell progeny. This twenty-four hour infusion would also insure minimal fluctuations in levels of amphipathic antioxidants.

Dosages for aerosol or intravenous administration would be adjusted based on T cell count, symptoms, response and patient tolerance to the medications. A loading dose may be necessary which would require higher initial dosages. Other free radical diseases may require substantially higher doses of particular amphipathic antioxidants. Dosage requirements are dependant upon the stage of the disease, fat composition, where the majority of the free radicals were generated and the primary organ which it effects. Further clinical experimentation will elucidate a more exacting dosage regimen.

Example 8

Trauma (Pathological Insult, see FIG. 13)

Given a 49 year old woman who is involved in a head on collision with another automobile. She sustains head trauma. When she arrives at the hospital they immediately administer an AMAOX solution intravenously. It is postulated that the AMAOX solution would markedly decrease the cerebral edema due to inflammation (which free radicals are involved in) and the tissue damage which occurs due to free radical damage. It is postulated that the patient would have an improved clinical course and that antioxidants in high dosages would have a similar effect as would steroids (which are routinely administered for severe head trauma today in real clinical cases). Steroids were proven to be potent antioxidants by Seligman, M. et. al. (Photochem. Phtobiol. 29: 549–58, 1979) and Demopoulos, H. B., et al. (Can J. Physiol. Pharmacol. 60: 1415–24, 1982).

Example 9

Sun Tan Lotion

AMAOX can be used as an additive to sun tanning lotions. Beta-carotene particularly has a photoprotective effect (likely by virtue of its characteristic of being an antioxidant). The other antioxidants also serve to increase the antioxidant levels in skin in an effort to limit free radical damage secondary to intense ultraviolet light exposure (which takes place during sun bathing). It is postulated that the amount of burning (tissue damage), pain (which is probably due to prostaglandins), and wrinkling of skin (tissue damage) can be limited as a result of increased antioxidant levels in skin.

| suntan lotion (10 ounces) | AMAOX | Amounts |
|---|---|---|
| | Vitamin E | 3000 mg |
| | Beta-carotene | 1500 mg |
| | Glutathione | 500 mg |
| | Vitamin C | 500 mg |

Example 10

Spinal Cord Trauma (See FIG. 13)

Given a 15 year girl who jumped off of a diving board into a shallow part of a swimming pool. Her head strikes the bottom of the pool. After being subsequently rescued she is no longer able to use her hands nor move her feet. X-rays show that she has sustained a fracture in her neck (cervical spine vertebrae 6). As soon as the diagnosis of quadriplegia is made by her physicians AMAOX are administered. It is postulated that by increasing the AMAOX levels that it would limit the damage done by free radicals, known to occur in spinal cord trauma (Demopoulos, H. B. et al.: Spinal Cord Injury, NE. Naftchi (ed), Spectrum Publications, Inc., New York, 1982, pp 45–64). Steroids are presently administered in real clinical situations for such cases.

| For Spinal Cord Trauma | AMAOX | Concentrations Intravenous Topical |
|---|---|---|
| | Vitamin E | 5 g/Kg/day |
| | | 1 Kg/M$^2$/day |
| | Beta-carotene | 2 g/Kg/day |
| | | 1 Kg/M$^2$/day |
| | Vitamin C | 0.5 g/Kg/day |
| | | 2 Kg/M$^2$/day |
| | Glutathione | 0.5 g/Kg/day |
| | | 1 Kg/$^2$/day |
| | Selenium | 5 ug/Kg/day |
| | Copper | 1 g/Kg/day |
| | Zinc | 2 mg/Kg/day |
| | Manganese | 1.3 mg/Kg/day |

**Copper, Manganese, Zinc and Selenium should only be given for two days intravenously.

Example 11

Cerebral Ischemia (See FIG. 13)

Routinely AMAOX would be given prior to surgery involving neurosurgical procedures. Given a 35 year old woman having a brain biopsy done in an effort to make a diagnosis of a particular type of brain tumor. During this routine procedure, her heart stops (cardiac arrest). The operative team is not able to resuscitate her for over ten minutes. After twelve minutes the heart begins to function normally. During this procedure her brain would have sustained cerebral ischemia (low oxygen content in the brain). Usually such trauma leaves the patient profoundly effected, and frequently non-functional. Free radicals have been shown to occur in cerebral ischemia animal models (Flamm, E. S., et. al.: Neural Trauma, Seminars in Neurological Surgery, vol. IV. A. J. Popp. et al. (editors). Raven press, New York, 1979, pp 289–96; Demopoulos, H. B. et al.: Anesthesia and Neurosurgery. 2nd edition. James E Cotrell and Herman Turndof (eds). The C. V. Mosby Company, St. Louis. 1986, pp 246–279). It is postulated that since antioxidant levels are significantly elevated prior to the cerebral ischemic injury that free radicals occurring would have their effect significantly reduced. Subsequently the patient would have less brain injury and have a much improved clinical outcome.

| For Cerebral Ischemia | AMAOX | Concentrations Intravenous Topical |
|---|---|---|
| | Vitamin E | 5 g/Kg/day |
| | | 1 Kg/M$^2$/day |
| | Beta-carotene | 2 g/Kg/day |
| | | 1 Kg/M$^2$/day |
| | Vitamin C | 0.5 g/Kg/day |
| | | 2 Kg/M$^2$/day |
| | Glutathione | 0.5 g/Kg/day |
| | | 1 Kg/$^2$/day |
| | Selenium | 5 ug/Kg/day |
| | Copper | 1 g/Kg/day |
| | Zinc | 2 mg/Kg/day |
| | Manganese | 1.3 mg/Kg/day |

**Copper, Manganese, Zinc and Selenium should only be given for two days intravenously.

The present invention relates to a free radical quenching composition comprising a liposome containing at least two members from the following: beta-carotene, vitamin E, vitamin C, glutathione, niacin, and at least one trace metal. The free-radical quenching composition preferably contains beta-carotene, vitamin E, vitamin C, glutathione, and niacin, and optionally at least one trace metal. The trace metal is Zn, Se, Cr, Cu, Mn, or mixtures thereof.

A cream, lotion, injectable solution, or a tablet can contain the above-described composition and a pharmaceutically acceptable carrier.

An effective amount of the above-described composition and optionally a pharmaceutically acceptable carrier can be used to deliver non-enzymatic antioxidants to a site in need thereof, to reduce the undesirable side effects of free radicals in a mammal in need thereof, to treat inflammatory conditions (such as rheumatoid arthritis and other autoimmune diseases) in a mammal in need thereof, to increase the level of antioxidants in mammalian cells (e.g. red blood cells, macrophages, lymphocyte, etc.) in need thereof, or to increase the level of antioxidants in mammalian cells and/or organs which are ex situ awaiting transplantation in need thereof.

AMAOX can be used in cases where free radicals have been implicated as part of the pathogenesis of a disease process. In some disease processes certain oxidants play a larger role than others; for example, the activation of collagenase from the latent form to the active form is by hydrogen peroxide and subsequently hypochlorous. If it was desired that only these particular oxidants would be eradicated by the selective use of particular antioxidants, only glutathione and ascorbic acid could be used since it has been pointed out that each antioxidant has a specific free radical which they can reduce. This is a feature which further differentiates this composition from the prior art. In the prior art there is no elucidation of which free radicals are to be eradicated.

Further variations and modifications of the foregoing will be apparent to those skilled in the art and such variations and modifications are attended to be encompassed by the claims that are appended hereto.

What is claimed:

1. A method of preventing or treating a disease or an injury induced by pathological free radical reactions, the method comprising administering to the mammal an effective amount of an antioxidant composition comprising:
   (i) a population of liposomes suitable for undergoing peroxidation and lysis; and
   (ii) at least two non-enzymatic amphipathic antioxidants selected from the group consisting of: beta-carotene, vitamin E, vitamin C, glutathione, niacin, and N-acetyl-cysteine, in an amount of sufficient to deliver 0.005–1.0 g beta-carotene per kg body weight, 0.001–10 g vitamin E per kg body weight, 0.001–2.0 g vitamin C per kg body, 0.001–2.0 g glutathione per kg body weight, 1–1000 mg niacin per kg body weight and 0.003–6.0 g N-acetyl-cysteine per kg body weight, wherein the disease or injury is selected from the group consisting of: acute respiratory distress syndrome, ischemia-reperfusion injury, hemorrhagic shock, tissue injury induced by inflammation, and tissue injury induced by a chemical agent or a caustic agent, and wherein the amphipathic antioxidant composition quenches free radicals and reduces the damage induced by the pathological free radical reactions.

2. The method of claim 1, wherein said composition further comprises at least one trace metal.

3. The method of claim 2, wherein said at least one trace metal is selected from the group consisting of zinc, selenium, chromium, copper and manganese.

4. The method of claim 1, wherein said composition further comprises a pharmaceutically acceptable carrier.

5. The method of claim 1, wherein said composition is administered by a route of administration selected from the group consisting of: intravenous, intraperitoneal, subcutaneous, intramuscular, intraarticular, intraarterial, intracerebral, intracerebellar, intrabronchial, intrathecal, topical, and aerosol route.

6. The method according to claim 2, wherein the composition includes an amount of trace metals sufficient to deliver 1–1000 µg trace metals per day.

7. A method for alleviating the deleterious effects of pathological free radical reactions in a mammal afflicted with a disease or an injury induced by pathological free radical reactions, the method comprising administering an effective amount of an antioxidant composition comprising:

(i) a population of liposomes suitable for undergoing peroxidation and lysis; and (ii) at least two non-enzymatic amphipathic antioxidants selected from the group consisting of: beta-carotene, vitamin E, vitamin C, glutathione, niacin, and N-acetyl-cysteine, in an amount of sufficient to deliver 0.0005–1.0 g beta-carotene per kg body weight, 0.001–10 g vitamin E per kg body weight, 0.001–2.0 g vitamin C per kg body, 0.001–2.0 g glutathione per kg body weight, 1–1000 mg niacin per kg body weight and 0.003–6.0 g N-acetyl-cysteine per kg body weight, wherein the disease or injury is selected from the group consisting of: acute respiratory distress syndrome, ischemia-reperfusion injury, hemorrhagic shock, tissue injury induced by inflammation, and tissue injury induced by a chemical agent or a caustic agent, and wherein the amphipathic antioxidant composition quenches free radicals and reduces the damage induced by the pathological free radical reactions.

8. The method of claim 7, wherein said composition further comprises at least one trace metal.

9. The method of claim 8, wherein said at least one trace metal is selected from the group consisting of zinc, selenium, chromium, copper and manganese.

10. The method of claim 7, wherein said composition further comprises a pharmaceutically acceptable carrier.

11. The method of claim 7, wherein said composition is administered by a route of administration selected from the group consisting of: intravenous, intraperitoneal, subcutaneous, intramuscular, intraarticular, intraarterial, intracerebral, intracerebellar, intrabronchial, intrathecal, topical, and aerosol route.

12. The method according to claim 7, wherein the composition includes an amount of trace metals sufficient to deliver 1–1000 µg trace metal per day.

* * * * *